(12) United States Patent
Brostrom et al.

(10) Patent No.: US 9,096,494 B2
(45) Date of Patent: *Aug. 4, 2015

(54) ARACHIDONIC ACID ANALOGS AND METHODS FOR ANALGESIC TREATMENT USING SAME

(71) Applicant: Cytometix, Inc., Bayside, WI (US)

(72) Inventors: Lane Brostrom, Bayside, WI (US); John R. Falck, Dallas, TX (US)

(73) Assignee: CYTOMETIX, INC., Bayside, WI (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/158,064

(22) Filed: Jan. 17, 2014

(65) Prior Publication Data

US 2014/0135401 A1     May 15, 2014

Related U.S. Application Data

(60) Division of application No. 13/481,333, filed on May 25, 2012, now Pat. No. 8,658,632, which is a continuation-in-part of application No. PCT/US2010/058041, filed on Nov. 24, 2010.

(60) Provisional application No. 61/264,434, filed on Nov. 25, 2009.

(51) Int. Cl.
*C07C 233/09* (2006.01)
*C07C 237/22* (2006.01)
*C07C 275/20* (2006.01)

(52) U.S. Cl.
CPC ............ *C07C 233/09* (2013.01); *C07C 237/22* (2013.01); *C07C 275/20* (2013.01); *C07C 2101/02* (2013.01); *C07C 2101/04* (2013.01); *C07C 2101/08* (2013.01)

(58) Field of Classification Search
USPC ........................................................ 514/183
See application file for complete search history.

*Primary Examiner* — Jeffrey S Lundgren
*Assistant Examiner* — Zenab Olabowale
(74) *Attorney, Agent, or Firm* — Quarles & Brady, LLP

(57) ABSTRACT

The present invention provides arachidonic acid (AA) analogs and compositions containing those analogs as active agents for use in analgesic treatments. Various methods of manufacturing the inventive compounds are provided and pharmaceutical formulations, including injectable and oral dosages, are described. Certain analogs are additionally useful as antipyretic compositions and in related fever reducing treatments.

4 Claims, 7 Drawing Sheets

CMX020

AM404

ARACHIDONIC ACID ANALOGS AND METHODS FOR ANALGESIC TREATMENT USING SAME

CROSS-REFERENCE TO RELATED APPLICATIONS

This is a divisional application which claims priority to U.S. application Ser. No. 13/481,333, filed May 25, 2012, which is a continuation-in-part application claiming priority to International Application PCT/US2010/058041, filed Nov. 24, 2010, which claimed the benefit of U.S. Provisional application 61/264,434, filed Nov. 25, 2009, all of which are incorporated by reference herein in their entirety for all purposes.

STATEMENT REGARDING FEDERALLY SPONSORED RESEARCH OR DEVELOPMENT

Not Applicable.

FIELD OF THE INVENTION

This invention relates to the treatment of pain. In particular this invention is directed to arachidonic acid (AA) analogs and their use in analgesic treatment.

BACKGROUND OF THE INVENTION

The pain pathway begins in the periphery with nociceptors that innervate skin, muscle, tendon or bone targets. Activated or sensitized nociceptors transmit noxious information to the spinal dorsal horn where spinal neurons then transmit information to rostral centers in the thalamus, reticular formation and midbrain. Other neurons carry the information to the somatosensory cortex where pain is interpreted. Nociceptive information transmitted through the spinal cord is heavily modulated by central neurons whose axons descend from the midbrain and other rostral areas to the spinal cord, and these descending pathways can be either inhibitory or facilitory.

Neurons contain a variety of voltage-gated ion channels. The voltage-gated K+ and Na+ channels regulate the excitability of neuronal cells and play a crucial role in setting the perceptual threshold of pain. The ability to modulate the activity of K+ or Na+ ion channels in neuronal cells is important for regulating the transmission of pain signals.

Epoxyeicosatrienoic acids (EETs) are produced from arachidonic acid via cytochrome P450 (CYP) epoxygenases. EETs regulate inflammation, angiogenesis, cellular proliferation, ion transport and steroidogenesis. In many issues, EET levels are regulated, inter alia, through their metabolism to vic-diols (vic-dihydroxyeicosatrienoic acids; DiHETrE) via the enzyme soluble epoxide hydrolase (EPHX2).

While some types of pain are effectively managed with opioids such as morphine or non-steroidal anti-inflammatory drugs (NSAIDS) such as aspirin or ibuprofen, opioids and NSAIDS both have numerous undesirable side effects. For instance, opioids frequently cause dependence and withdrawal problems in users. The use of opioids in the management of pain is further limited due to impairment of Na+/K+-ATPase activity after opiate treatment, a possible mechanism of tolerance/addiction. Similarly NSAIDS can cause hypertension, ulcer perforation, upper gastrointestinal bleeding and even death in severe cases.

Acetaminophen is one of the most widely used drugs in the world for treatment of pain and fever; probably the most commonly prescribed medicine in children. Over 600 products contain acetaminophen including OTC pain, cold and flu remedies and prescription medications like Vicodin. It has a unique position among analgesic drugs. Unlike NSAIDs, it is considered an ineffective anti-inflammatory, but does not produce gastrointestinal damage or untoward cardio-renal effects; unlike opiates, it is ineffective in pain arising from smooth muscle spasm, but has no depressant effect on respiration. The acetaminophen metabolite that produces analgesia is AM404—now known to provide analgesia through CB1 and TRPV1 receptors. FIG. 1 illustrates the metabolism of acetaminophen to AM404 and, in addition, the less desirable molecule NAPQI. Unfortunately acetaminophen is toxic in high doses and is responsible for the majority of the acute liver failure cases in the United States. NAPQI is the molecule largely believed to be responsible for liver failure.

Accordingly, a need exists for improved analgesic treatment that avoids the above-mentioned side effects but provides an effective and safe treatment for pain.

SUMMARY OF THE INVENTION

Here, the inventors demonstrate novel compositions of arachidonic acid analogs and methods of use thereof for treatment of pain. The invention is based, in part, on the understanding that arachidonic acid (AA) and other polyunsaturated fatty acids including eicosapentaenoic acid (EPA) and docosahexaenoic acid (DHA) are catalyzable substrates for cytochrome P450 epoxygenase (CYP4X1) in neurons. AA, for example, is converted to four regioisomers of EETs (i.e., 5,6-EET; 8,9-EET; 11,12-EET and 14,15-EET) by CYP4X1, and application of nanomolar concentrations of EETs (e.g., 11,12-EET) induces suppression of the outward K+ current and inward Na+ current, effectively altering the cellular membrane potential and polarization in neurons. EETs (or other P450 epoxygenase-derived epoxides) and certain selected agonist analogs may therefore regulate neuronal function and contribute to the modulation and treatment of pain.

Accordingly, the invention encompasses in a first aspect certain compounds having the structure:

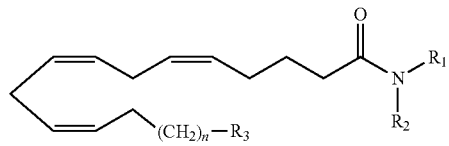

wherein: $R_1$ is H, or a $C_1$-$C_6$ alkyl, $C_2$-$C_6$ alkenyl, $C_3$-$C_6$ cycloalkyl or $C_3$-$C_6$ cycloalkenyl which is unsubstituted or substituted with at least one hydroxyl group; and $R_2$ is H, or a $C_1$-$C_3$ alkyl; $C_3$-$C_6$ cycloalkyl; or $R_1$ and $R_2$ form a $C_3$-$C_6$ heterocyclic ring with the nitrogen bonded to said $R_1$ and $R_2$; wherein any carbon constituent of $R_1$ or $R_2$ can be replaced by O, S, or R'N wherein R' is H or a $C_1$-$C_6$ alkyl; $R_3$ is

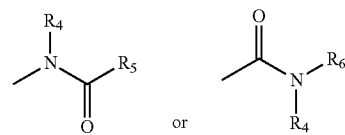

in which:

$R_4$ is H, or a $C_1$-$C_6$ alkyl, $C_2$-$C_6$ alkenyl, $C_3$-$C_6$ cycloalkyl or $C_3$-$C_6$ cycloalkenyl; $R_5$ is a $C_1$-$C_6$ alkyl, $C_3$-$C_6$ cycloalkyl, or $C_1$-$C_6$ alkoxy, or $C_2$-$C_6$ alkyl ether which is unsubstituted or substituted with one or more of hydroxyl, phenyl, phenyloxy, or fluorine, or $R_5$ is $NR_7R_8$, or $C(O)NR_7R_8$ in which $R_7$ and $R_8$ are independently selected from H, a $C_1$-$C_6$ alkyl, $C_2$-$C_6$ alkenyl, $C_3$-$C_6$ cycloalkyl, or $C_3$-$C_6$ cycloalkenyl group; $R_6$ is H, or a $C_1$-$C_6$ alkyl, $C_2$-$C_6$ alkenyl, $C_3$-$C_6$ cycloalkyl, or $C_3$-$C_6$ cycloalkenyl group; wherein any carbon constituent of $R_4$, $R_5$, $R_6$, $R_7$ or $R_8$ can be replaced by O, S, or R'N wherein R' is H or a $C_1$-$C_6$ alkyl; and n is 0, 1 or 2; or a pharmaceutically acceptable salt thereof.

Exemplary compounds encompassed by the invention include:

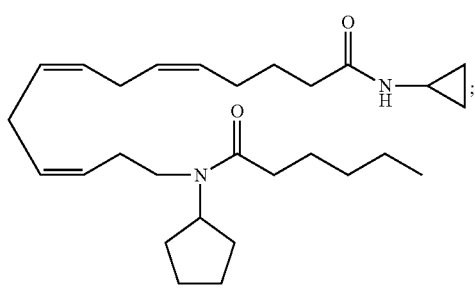

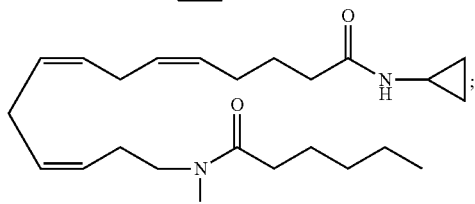

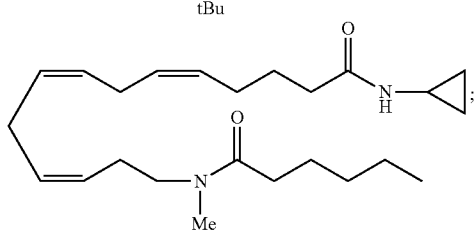

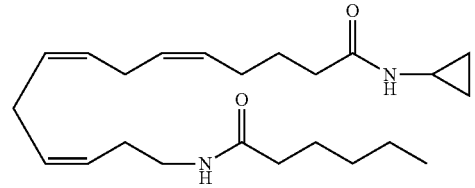

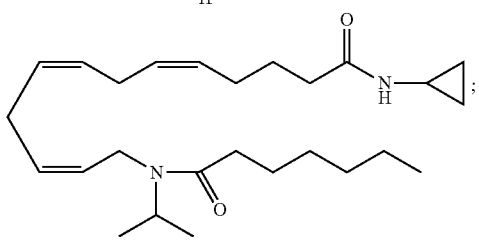

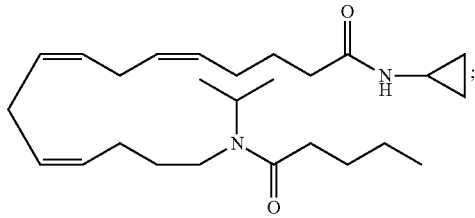

-continued

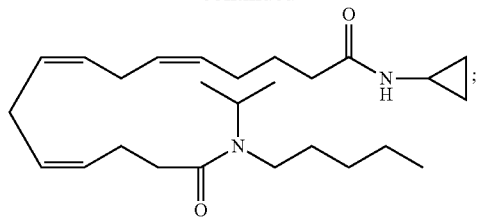

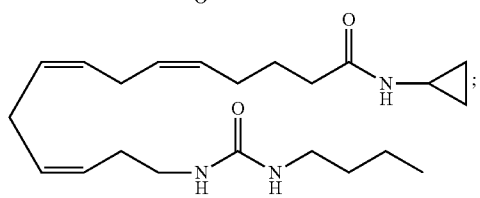

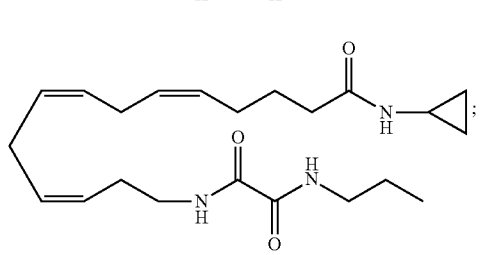

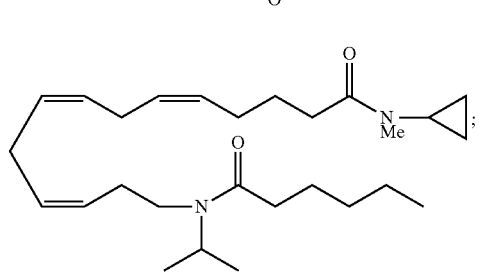

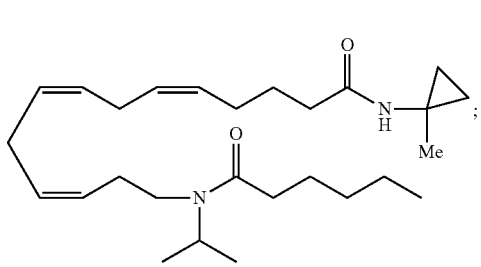

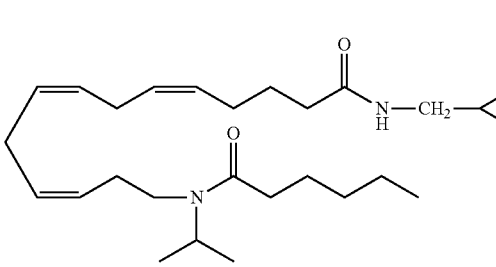

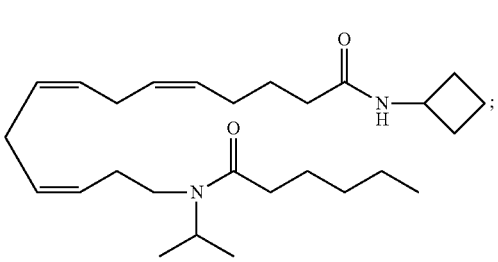

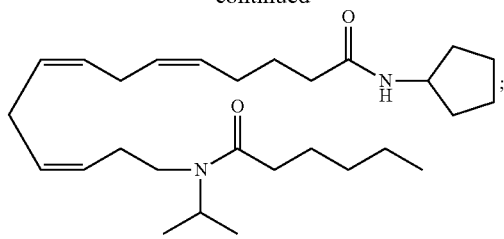

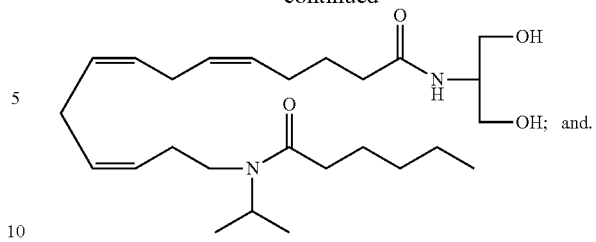

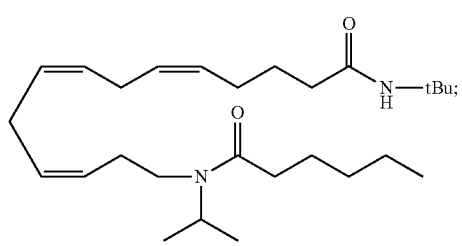

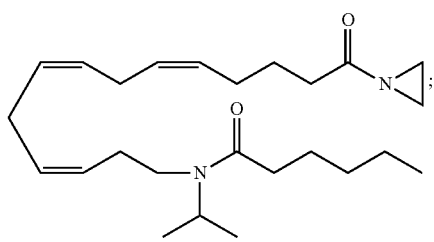

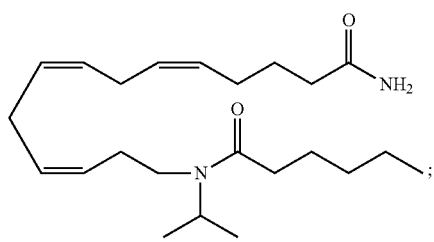

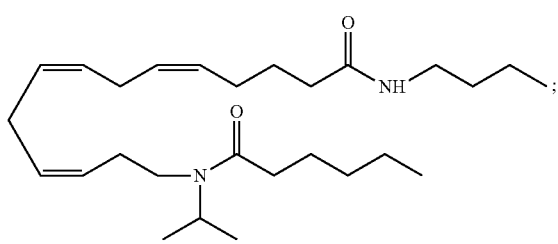

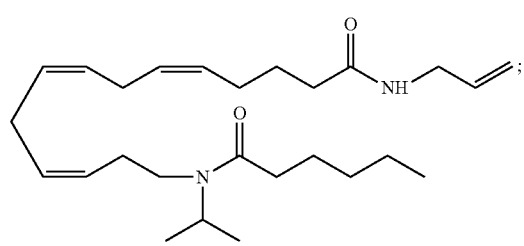

A particularly preferred compound according to the invention has the structure:

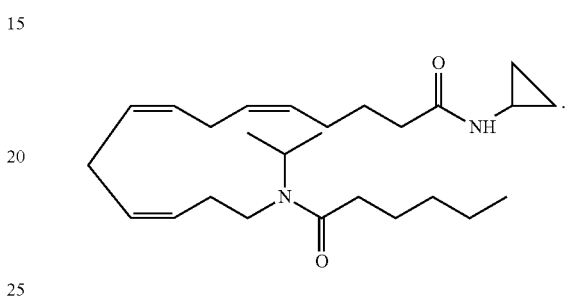

Compounds according to the invention are, in certain embodiments, provided in the form of a composition comprising a compound as described and claimed herein in combination with a pharmaceutically acceptable carrier. Particularly preferred compositions are in the form of injectable dosages or oral dosages. Certain compositions of the invention may be provided in the form of oil-in-water emulsions, while other compositions may be in form of anhydrous emulsions or lyophilized preparations. Compositions of the invention may, in certain delivery vehicle formulations, include a cyclodextrin with the compound.

In another aspect, the invention encompasses a kit for providing analgesia to a subject. Such a kit includes a compound as described and claimed herein and a delivery device to administer the compound to the subject.

The present invention further provides methods of providing analgesic treatment in a subject, particularly the reduction of pain in a subject. Such methods include steps of administering to a subject a therapeutically effective amount of a compound as described and claimed herein, whereby analgesia is provided to the subject. Administration may be performed by, e.g., intravenous injection in bolus or continuous infusion fashion, or by oral dosing with a tablet or capsule.

In yet another embodiment, the invention encompasses the use of AA analogs according to the invention for the manufacture of a medicament for providing analgesia in a subject. As well, the present invention further contemplates compounds according to the invention for use in providing analgesia in a subject.

The invention further provides a method of reducing fever in a subject. Such a method includes the step of administering to a subject a therapeutically effective amount of a compound described and claimed herein, whereby fever is reduced in the subject. Of course, the invention encompasses methods of using an inventive compound for the manufacture of a medicament for reducing fever in a subject.

In another aspect, the invention provides a method of synthesizing an inventive compound that includes steps of:

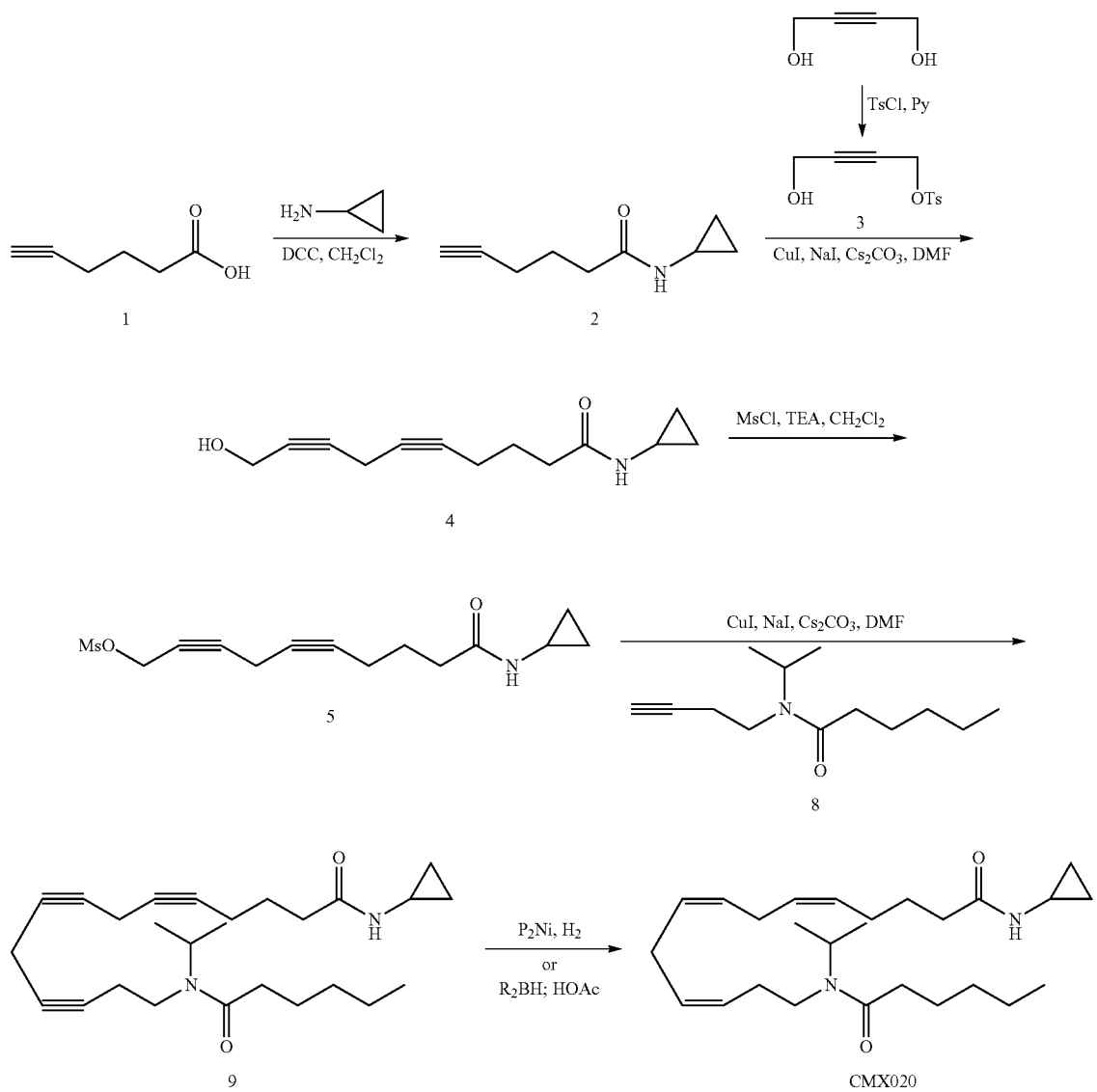
thereby providing a compound according to the invention.
Another method of providing an inventive compound includes steps of:
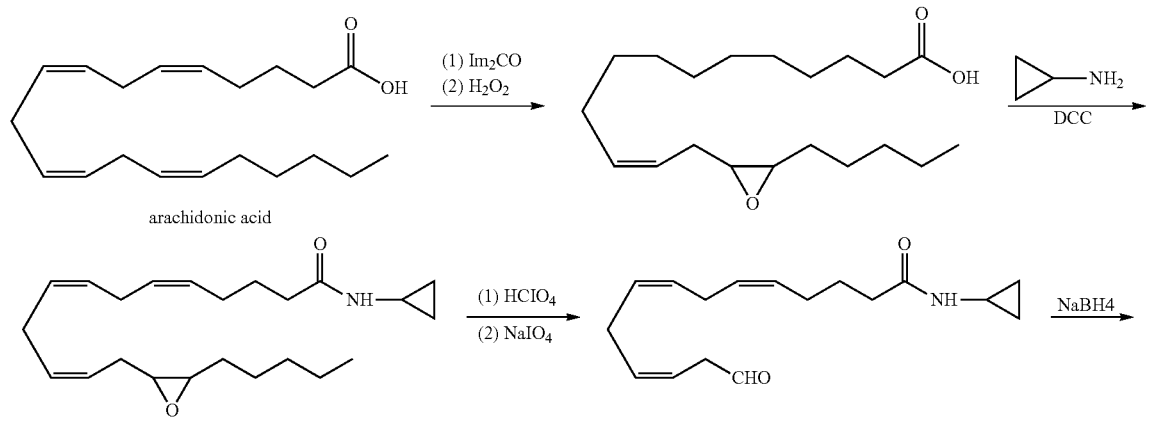

-continued

CMX-020

In yet another aspect, the invention encompasses certain compounds having the structure:

wherein:

$R_1$ is H, or a $C_1$-$C_6$ alkyl, $C_3$-$C_6$ alkenyl, $C_3$-$C_6$ cycloalkyl or $C_3$-$C_6$ cycloalkenyl which is unsubstituted or substituted with a hydroxyl group or a $C_1$-$C_6$ alkyl;

$R_2$ is H, or a $C_1$-$C_3$ alkyl; or $R_1$ and $R_2$ form a $C_3$-$C_6$ heterocyclic ring with the nitrogen bonded to said $R_1$ and $R_2$;

$R_3$ is:

in which:

$R_4$ is H, or a $C_1$-$C_6$ alkyl, $C_3$-$C_6$ alkenyl, $C_3$-$C_6$ cycloalkyl or $C_3$-$C_6$ cycloalkenyl;

$R_5$ is a $C_1$-$C_6$ alkyl, $C_1$-$C_6$ alkoxy, or $C_2$-$C_6$ alkyl ether which is unsubstituted or substituted with one or more of hydroxyl, phenyl, phenyloxy, or fluorine, or $R_5$ is $NR_2R_8$; or $C(O)NR_7R_8$ in which $R_7$ and $R_8$ are independently selected from H, a $C_1$-$C_6$ alkyl, $C_3$-$C_6$ alkenyl, $C_3$-$C_6$ cycloalkyl or $C_3$-$C_6$ cycloalkenyl;

$R_6$ is H, or a $C_1$-$C_6$ alkyl, $C_3$-$C_6$ alkenyl, $C_3$-$C_6$ cycloalkyl or $C_3$-$C_6$ cycloalkenyl;

n is 0, 1, 2, 3, or 4;

position a is —$CH_2$—, —$CH(CH_3)$—, —$C(CH_3)_2$—, O or $NR_9$ where $R_9$ is H, OH, or a $C_6$ alkyl;

position b is —$CH_2$—, —$CH(CH_3)$—, —$C(CH_3)_2$—, O, S, or $NR_{10}$ where $R_{10}$ is H, OH, or a $C_1$-$C_6$ alkyl; wherein position a and b are not both heteroatoms;

m is 0, 1, 2, 3, or 4; wherein when m is 0, then position b is a carbon;

p is 1, 2, or 3; or a pharmaceutically acceptable salt thereof.

The presently-described and claimed compounds and methods provide various advantages over prior compounds and methods in that they provide for analgesic effect with a reduction in the side effects encountered with prior analgesics.

Other objects, features and advantages of the present invention will become apparent after review of the specification, claims and drawings.

DETAILED DESCRIPTION OF THE INVENTION

I. In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

Figure 3:
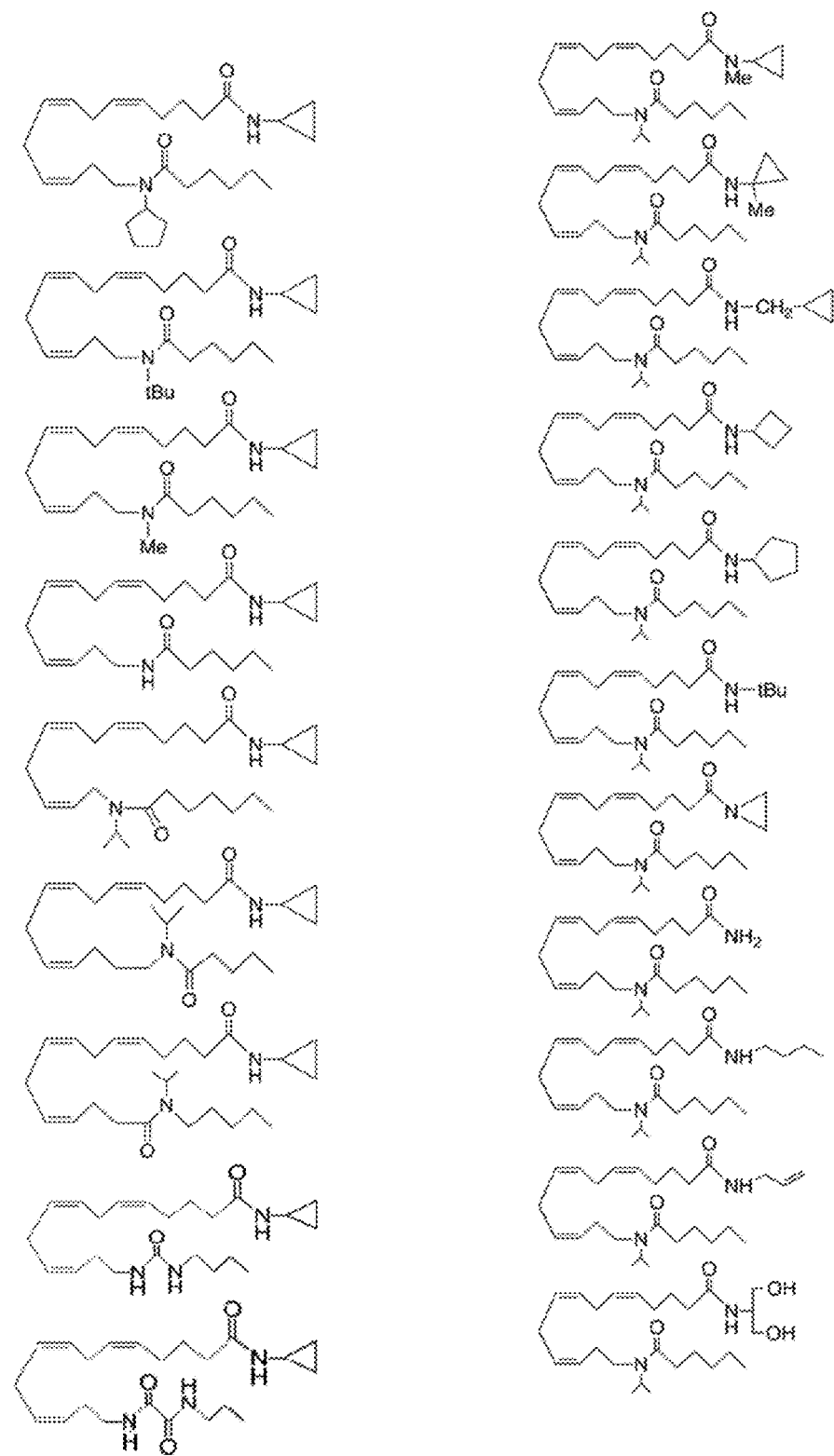
FIG. 3 provides exemplary AA analogs of the invention including the compound CMX-020.

Arachidonic acid (AA) analogs of the invention have analgesic effects similar to morphine and other opioid analgesics. However, these compounds have a different mechanism of action than opioid analgesics. The inventors° preliminary tests have shown that AA analogs do not have the addiction side effects common in many conventional pain treatments. As well, preliminary results show that a number of different delivery options are possible, including brain injections, DRG injections, intraperitoneal injections, intranasal administration, blood injections, transdermal, or oral delivery. Chemical analogs of AA may be engineered or particularly delivered to have a more sustained effect than traditional analgesics. Liposomes, mycelles, cyclodextrins, and emulsifiers can be used in to make AA analog preparations more soluble and easier to administer and/or more stable. A particularly preferred AA analog described herein is designated CMX-020, which is chemically similar to the 14,15-EET (epoxyeicosatrienoic acid). The 14,15-EET was observed to be the most potent analgesic of the natural EETs. However, CMX-020 is a much more potent and longer lasting analgesic than the natural 14,15-EET. The present invention further encompasses chemical variations based on CMX-020, which are envisioned to be useful in analgesic treatment (exemplary such compounds are illustrated in FIG. 3). The present compounds, including CMX-020, have also demonstrated fever reducing effects and are further envisioned to find use as antipyretic compositions and in fever reducing therapies.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a compound of the present invention into the body, preferably into the systemic circulation. Examples include but are not limited to oral, nasal, otic, ophthalmic, buccal, sublingual, pulmonary, transdermal, transmucosal, as well as subcutaneous, intraperitoneal, intravenous, epidural and intramuscular injection.

A "therapeutically effective amount" means an amount of a compound that, when administered to a subject for treating a disorder, condition, or disease, is sufficient to effect such treatment for the disorder, or condition, or disease. The "therapeutically effective amount" will vary depending on the compound, the disorder, or condition, or disease state being treated, the severity or the disorder, or condition, or disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 2 milligrams to about two grams of the active ingredient, and preferably comprises from about 10 milligrams to about 1.0 gram of the active ingredient.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing, device, a syringe, a needle, a tampon, or a dosage-measuring container. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The compounds of the present invention, optionally comprising other pharmaceutically active compounds, can be administered to a patient either orally, rectally, parenterally, (thr example, intravenously, intramuscularly, or subcutaneously) intracisternally, intravaginally, intraperitoneatly, intravesically, epidurally, ophthalmically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques. For example, the compositions of the present invention can be administered to a subject by brain (via vPAG) injections, intrathecal injections, intraperitoneal injections, or blood injections.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampoules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily (emulsion) suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using anon-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The compounds according to the present invention may also contain adjuvants such as preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin. In particular, liposomes, mysomes and emulsifiers can be used in to make the present compounds more soluble for delivery.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), polyanhydride, a poly(beta-hydroxy-butyrate), a poly(orthoester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the compounds of the present invention can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions of the present invention may further include a cyclodextrin component in order to, e.g., improve water solubility of an active pharmaceutical ingredient, prolong drug release, and improve tabletting characteristics. In general, cyclic structure oligomers of glucose ("cyclodextrin") are obtained from the starch digests of certain bacteria. The most abundant cyclodextrins are alpha, beta and gamma cyclodextrin which have 6, 7 and 8 glucose units, respectively. The interior cavity of a cyclodextrin is hydrophobic and the exposed surface of the molecule is hydrophilic. Cyclodextrins are known to enhance active pharmaceutical ingredient stability, aqueous solubility, and reduce volatility. Some examples of commercially available cyclodextrin, or derivatives thereof, are as follows: alpha-Cyclodextrin (CAS #: 10016-20-3); (2-Hydroxypropyl)-alpha-cyclodextrin (CAS #: 128446-33-3); beta-Cyclodextrin (CAS #: 7585-39-9); 6-O-alpha-D-Glucosyl-beta-cyclodextrin (CAS #: 92517-02-7); gamma-Cyclodextrin (CAS #: 17465-86-0); and (2-Hydroxypropyl)-gamma-cyclodextrin (CAS #: 128446-34-4). Cyclodextrins particularly useful in formulating a delivery vehicle to administer the present compounds include: the sulfobutyl ether beta-cyclodextrin (SBE-beta-CD) available from Cydex Pharmaceuticals, Inc. under the tradename CAPTISOL; and the cyclodextrin and hydroxypropyl betacyclodextrins available from Roquette Pharma under the tradename KLEPTOSE. An exemplary intravenous formulation may be formulated in saline water containing 0.9% sodium chloride, 450 mg/mL, of CAPTISOL cyclodextrin, and 1.5 mg/mL of the compound designated CMX-020 described and claimed herein.

Compositions for rectal or vaginal administration can be prepared by mixing a compound of the present invention and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active ingredient. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a compound according to the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methyl hydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compounds of the present invention may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The compounds of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient, with 1-10 mg a preferred dosage. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compounds of the present invention are administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the compounds.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician, dentist, or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

The compounds of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended fix parenteral use.

Five distinct classes of injections exist as defined by the LISP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The invention further contemplates formulating combination pharmaceutical compositions which include both a compound as described and claimed herein and an anesthetic agent. Such compositions are useful in medical procedures including, but not limited to, general anesthesia, sedation for mechanically ventilated subjects, and procedural sedation. In general, an "anesthetic agent" is a drug that brings about a state of anesthesia in a subject. However, while many current anesthetic agents produce unconsciousness, they provide no analgesia and must be used in combination with other drugs. For example, propofol is approved in more than fifty countries, and generic versions are available. Propofol is regularly administered in combination with opioids, such as fentanyl, alfentanil, remifentanil and sufentanil, to provide combination hypnotic effect and pain alleviation. As can be appreciated, compounds of the present invention are suitable for replacing such opioid analgesics in combination anesthetic/analgesic formulations and for use in related medical procedures. A variety of anesthetic agents may be used in combination with the present compounds, including intravenous agents such as barbiturates, benzodiazepines, etomidate, ketamine and propofol. In one embodiment, the analgesic compound designated CMX-020 is combined in a pharmaceutical composition with propofol, (available from Astra Zeneca under the tradename DIPRIVAN) to provide an intravenously administered formulation providing both hypnotic and analgesic effects.

Various exemplary embodiments of compositions and methods according to this invention are now described in the following examples. In these embodiments, specific products identified by Arabic numerals (e.g., 1, 2, 3, etc.) refer to the specific structures so identified in the following description. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Characterization of CMX-020

Figure 1:
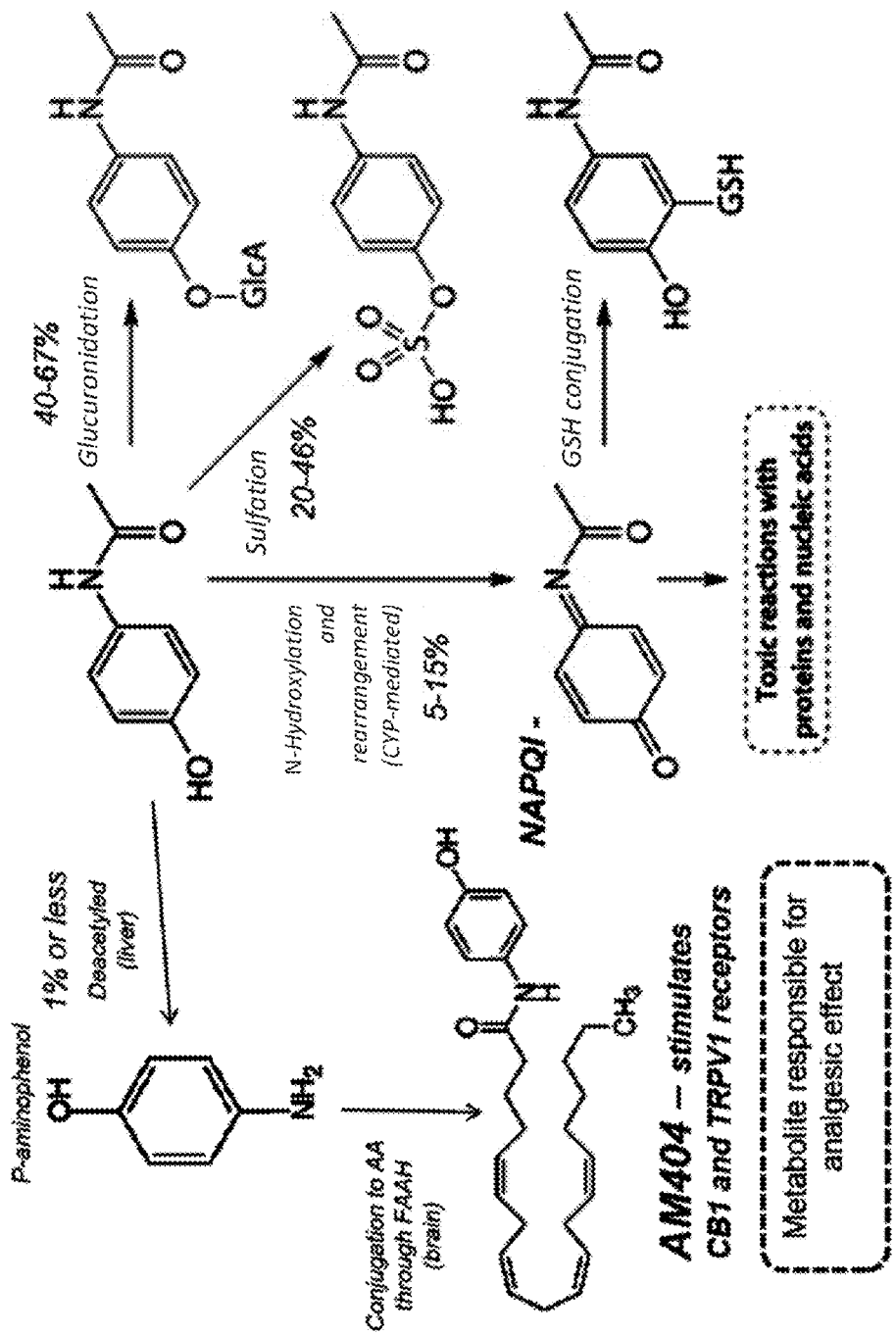
FIG. 1 depicts a general schematic illustrating acetaminophen metabolism.
Figure 2:
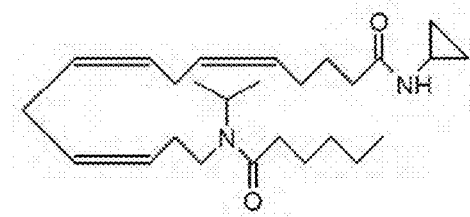
FIG. 2 illustrates the chemical structures of CMX-020 and the acetaminophen metabolite AM404.
Figure 2:
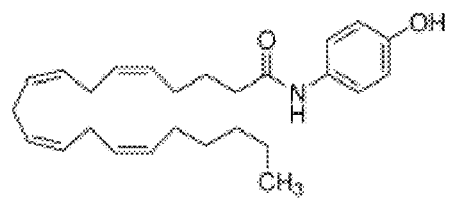

The present example describes the characterization of compound CMX-020, which is depicted in FIG. 2, as is AM-404.

CMX-020 Binding Assay Results.

CMX-020 was tested in the Cerep Full BioPrint Profile, which is a panel of 158 different in vitro receptor binding and enzyme assays. For the initial BioPrint screen, a free compound concentration of 10 µM was used, which corresponds to a 2.5 mg/kg bolus dose in a mouse. When injected the CMX 020 lipid therapeutic becomes partially bound to plasma or serum proteins; our analysis also shows approximately 99% of CMX-020 is bound. Thus, a 2.5 mg/kg bolus dose would be equivalent to a 0.1 µM free compound concentration. For the BioPrint Assay, any receptor binding or enzyme assays that display inhibition over 50%, at a CMX-020 concentration of 10 µM, was singled out for further IC50 analysis. Table 1 below shows all receptors in the Cerep BioPrint Profile with inhibition over 50% along with their IC50 concentrations.

TABLE 1

CMX-020 - Assay Binding Summary (BioPrint/Cerep)

| Receptor | % Inhibition @10 uM | IC50(M) |
|---|---|---|
| CB1 Cannabinoid agonist | 98 | 2.10E−08 |
| CB2 Cannabinoid agonist | 98 | 1.50E−07 |
| MT1(ML1A) agonist-Melatonin | 88 | 1.20E−06 |
| A3 agonist-Adenosine A3 | 64 | 2.60E−06 |
| κ-opioid agonist | 61 | 4.70E−06 |
| CL-Channel (GABA gated) antagonist | 80 | 5.10E−06 |
| TRPV1(VR1) agonist | 59 | 7.50E−06 |
| PPRA-Peroxisome proliferator-activated | 58 | 7.80E−06 |
| δ- opioid agonist | 52 | 1.30E−05 |

Receptors Implicated in Dependence and Addiction.

Of the 158 receptors and enzymes screened in the BioPrint assay, 53 are selected by Cerep for implication in the dependence and addiction panel (see receptor and enzyme category table below). Out of the 53 receptors and enzymes implicated in dependence and addiction, CMX-020 had significant inhibition in only the cannabinoid and opioid receptors. The role of these receptors in dependence and addiction is discussed below.

CB1 Receptor in Dependence and Addiction.

It is well known that natural ligands for the CB1 cannabinoid receptors, anandamide and 2-arachidonylglycerol, affect nervous system functions such as reward, memory, cognition, and pain perception. The perceived role of CB1 receptors in dependence and addiction is driven largely by Δ9-THC, the active ingredient in marijuana, which is a popular recreational drug. It is believed that Δ9-THC produces dependency or addiction in two ways: by mimicking natural ligands for CB1 receptors and by producing elevated dopamine levels. In comparing dependence and addiction with other drugs however, marijuana does not have the same level of risk as opioids (e.g., morphine, heroin), cocaine, or alcohol. Unlike opioids, cocaine and alcohol, there is little risk in overdosing on marijuana. Also, the development of dependence on marijuana is much less prevalent than nicotine and cocaine. While CMX-020 is a strong CB1 receptor agonist, it is unlike Δ9-THC in that it does not elevate dopamine levels. CMX-020 is more like the active ingredient in Tylenol, AM404, which is both a CB1 and TRPV1 agonist, and which has no significant risk for dependence and addiction.

κ-Opioid and δ-Opioid in Dependence and Addiction.

Opioid receptors, μ, κ, δ (mu, kappa, and delta), are G protein-coupled receptors found in the central nervous system. Most traditional opioids used in pain management, like morphine and fentanyl, as well as the highly addictive opioid heroin, are μ-opioid receptor agonists. Interestingly, morphine's addictive properties are completely abolished in mice lacking the μ-opioid receptor. Thus, the μ-opioid receptor is responsible for the addictive effects of morphine and most other traditional opioids used in pain management. As the CMX-020 assay binding table above shows, CMX-020 is an active agonist of the κ-opioid and δ-opioid receptors, but not the μ-opioid receptor. The role of the δ-opioid receptor in reward and addiction is still poorly understood, but there is emerging evidence that the δ-opioid receptor is involved in opioid reward and addiction. Accordingly, CMX-020 is a relatively weak δ-opioid agonist—its IC50 concentration as a δ-agonist is nearly 3× lower than its value as a δ-agonist. But moreover, the κ-opioid receptor activation has been shown to produce aversive states, which should suppress any low-level, but unwanted δ-mediated risks of dependence and addiction.

The screening results of CMX-020 in the full BioPrint Profile (Cerep) provides important information on dependence and addiction. The primary concern for CMX-020 may be the cannabinoid and opioid agonist activity. Although CMX-020 is a strong CB1 agonist, it does not elevate dopamine levels like Δ9-THC. Its combination of CB1 and TRPV1 activity makes it similar to AM404, the active ingredient in Tylenol, which is proven to show no apparent risk for dependence and addiction. CMX-020 also shows agonist activity for the κ-opioid and δ-opioid receptors. This combination appears to constitute a unique non-habit forming alternative to traditional μ-opioids for the treatment of pain.

Table 2 below presents the Cerep BioPrint receptors and enzymes that are implicated in dependence and addiction, have been screened using CMX-020, but are not active.

TABLE 2

Receptors and Enzymes Implicated in Addiction but Not Active for CMX-020

| Group/Receptor | % Inhibition @10 uM |
|---|---|
| Non Peptide receptors Adenosine/A2A | 7 |
| Non Peptide receptors Dopamine/D1 | 7 |
| Non Peptide receptors Dopamine/D2S | 8 |
| Non Peptide receptors Dopamine/D3 | 25 |
| Non Peptide receptors GABA/GABAA | 11 |
| Non Peptide receptors GABA/GABAB(1b) | −6 |
| Non Peptide receptors Glutamate/AMPA | 9 |
| Non Peptide receptors Glutamate/kainate | −1 |
| Non Peptide receptors Glutamate/NMDA | −8 |
| Non Peptide receptors Glutamate/PCP | −6 |
| Non Peptide receptors Serotonin/5-HT1A | 26 |
| Non Peptide receptors Serotonin/5-Ht2A | 29 |
| Non Peptide receptors Serotonin/5-HT3 | −1 |
| Non Peptide receptors Sigma/Sigma non selective | 31 |
| Peptide receptors Cholecystokinin/CCK2 | −27 |
| Peptide receptors Melanocortin/MC4 | 0 |
| Peptide receptors Opioid/mu(MOP) | 26 |
| Peptide receptors Opioid/NOP(ORL1) | 5 |
| Nuclear receptors Steroid nuclear/GR | 9 |

TABLE 2-continued

Receptors and Enzymes Implicated in Addiction but Not Active for CMX-020

| Group/Receptor | % Inhibition @10 uM |
|---|---|
| Membrane ligand-gated GABA/GABBA | 11 |
| Ion channels Membrane ligand-gated Glutamate/AMPA | 9 |
| Ion channels Membrane ligand-gated Glutamate/kainate | −1 |
| Ion channels Membrane ligand-gated Glutamate/NMDA | −8 |
| Ion channels Membrane ligand-gated Glutamate/PCP | −6 |
| Ion channels Membrane ligand-gated Serotonin/5HT3 | −1 |
| Dopamine transporter/5HT transporter | 15 |
| Amine transporter-Dopamine/dopamine transporter | 15 |
| Amine transporter- Serotonin/5HT transporter | 10 |
| Non-kinase --ATPase/ATPase(Na+/K+) | 12 |

Example 2

Analgesic Effect of CMX-020 and Intravenous/Oral Formations

Based on the inventors research, CMX-020, is a rapidly acting intravenous analgesic that can be used as an adjunct to traditional opioids or as a stand-alone analgesic. Chemically, it is close structural analog of a set of lipid mediators derived from arachidonic acid that the body uses to control pain. Like acetaminophen, the analgesic effect of CMX-020 also appears to be produced through the CB1 and TRPV1 receptors. Side-by-side comparisons of AM404 with CMX-020 demonstrate that CMX-020 is a more potent analgesic without the toxic effects. Because CMX-020 does not have the toxic effects of acetaminophen, higher daily doses are possible. When higher doses are used, the analgesic effect is similar to morphine.

CMX-020 is very slightly soluble in water and, thus, is formulated in an opaque white, oil-in-water emulsion. When produced in bulk quantities, it contains 10 mg/ml of CMX-020, described here. In addition to the active component, CMX-020, a preferred isotonic formulation also contains, by weight, soybean oil (10%), glycerol (2.25%), Tween 80 (0.61%), hydrogenated phospholipid (0.49%) and disodium edetate (0.005%); with sodium hydroxide to adjust pH. CMX-020 provided as an Injectable Emulsion is isotonic and has a pH of 7-8.5. The structural formula for CMX-020 is, $C_{26}H_{44}N_2O_2$:

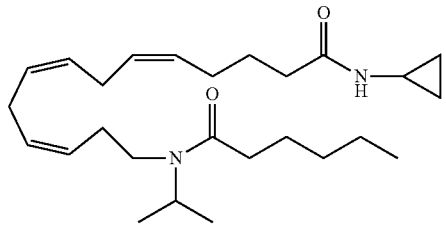 [SMILES: CCCCCC(=O)N(CC/C=C\C/C=C\C/C=C\CCCC(=O)NC1CC1)C(C)C]

Molecular weight: 416.64

The precise mechanism of the analgesic properties of CMX-020 has yet to be established and certainly no one mode of operation is adopted herein. However, like acetaminophen, the effects of CMX-020 appear to be mediated, in part, through cannabinoid and vanilloid receptors. Studies with $CB_1$ cannabinoid and TRPV1 vanilloid knockout mice (both homozygotes) show that the effect of CMX-020 is altered in both; but in $CB_1$ cannabinoid knockout mice, the analgesic effect of CMX-020 is almost completely blocked. Furthermore, the mechanisms appear unique and different from morphine, fentanyl, and NSAIDs.

CMX-020 provided as the Injectable Emulsion (1 mg/ml) is a fast-acting intravenous pain therapeutic that performs like morphine, providing high levels of analgesia, which can be established through dose titration. CMX-020 is apparently a more potent analgesic than acetaminophen, without the API chemistry that makes acetaminophen toxic to the liver. Accordingly, CMX-020 can function as an alternative to acetaminophen, an opioid-sparing therapeutic, or as an opioid replacement. Intravenous injection of a therapeutic dose of CMX-020 produces analgesia rapidly, usually within 3-5 minutes from the start of an injection. As with other rapidly acting intravenous agents, the half-time of the blood-brain equilibration is approximately 1 to 3 minutes, and this accounts for the rapid induction of analgesia.

CMX-020 provided as the injectable Solution provides onset of pain relief within 3-5 minutes after bolus injection or infusion and is appropriate for mild, moderate, or severe acute pain. The duration of effect from bolus injection is 20-30 minutes. A sustained analgesic effect is established using continuous infusion. The level of analgesic effect can be adjusted through dose titration. Sustained levels of analgesia can be maintained for 48 hours or more. Specific applications include: acute post operative pain management; breakthrough pain therapy; intensive care units; acute trauma; intravenous patient-controlled analgesia; and end of life pain control.

CMX-020 Injectable Solution may also be given to patients during surgery or dental procedures to relieve pain and as an adjunct to an anaesthetic. CMX-020 Injectable Solution also reduces fever within 30 minutes after the start of administration with duration of the antipyretic effect of at least 2 hours after ending administration.

Dosage and Analgesic Equivalence with Acetaminophen and Morphine has been determined by the inventors for CMX-020. Using the preclinical writhing assay in mice to establish relative levels of analgesia, the dose of CMX-020 that provides an equivalent (1x) level of analgesia to the recommended dose of intravenous acetaminophen (the equivalent of 1,000 mg in human) is a bolus injection of 0.01 mg/kg, followed by continuous infusion at a rate of 0.08 mg/kg/hr. The level of analgesia established by acetaminophen is not dose dependent. The level of analgesia established by CMX-020 is dose dependent. The doses of CMX-020 that correspond to higher levels of analgesia in comparison to acetaminophen in the mouse writhing assay (2x and 3x) are shown in Table 3 below.

TABLE 4

Analgesic Equivalence for a 70 kg human:
Dosing for CMX-020 and Morphine

|  | CMX-020 | Morphine |
|---|---|---|
| Bolus | 0.6 mg | 0.6 mg |
| Bolus | 1.4 mg | 1.4 mg |
| Bolus | 2.8 mg | 2.8 mg |
| Bolus | 5.6 mg | 5.6 mg |
| Maintenance | 6.0 mg/hr | 3.0 mg/hr |
| Maintenance | 11.0 mg/hr | 5.5 mg/hr |
| Maintenance | 23.0 mg/hr | 11.5 mg/hr |
| Maintenance | 45.0 mg/hr | 22.5 mg/hr |

CMX-020 can also be given in doses that provide equivalent analgesic levels to different doses of morphine, as shown in Table 4 above. For bolus injections, the analgesic effect of CMX-020 is equivalent to morphine on a mg/kg basis. For example, a 1 mg bolus dose of CMX-020 will establish roughly the same level of analgesia as a 1 mg bolus dose of morphine. However, CMX-020 will be faster acting (within 3-5 minutes for CMX-020 versus 20 minutes for morphine) and its analgesic effect will be shorter in duration (20-25 minutes for CMX-020 versus 35-40 minutes for morphine). To maintain a constant level of analgesia, a bolus injection should be followed by continuous infusion. To establish an analgesic equivalence with morphine via continuous infusion, twice the mg/kg dose of CMX-020 is required. For example, a 6 mg/hr infusion dose of CMX-020 is equivalent to a 3 mg/hr infusion dose of morphine. Like morphine, the dose of CMX-020 can be titrated over a wide range (see Table 3 above) to establish the patient required analgesic level.

Example 3

AA Analog Efficacy in Standard Pain Assays

In this example, the inventors compare the performance of intravenously delivered CMX-020 to both Perfalgan (intravenous acetaminophen) and morphine (the market leading intravenous opioid) in both the tail-flick and writhing assay. The tail-flick assay represents the most severe acute pain indications. The writhing assay is a more moderate pain assay that represents internal noxious pain indications, but also encompasses inflammatory, chemical, and persistent central

TABLE 3

Table 3. Dose Equivalence and Maximum Recommended Doses of CMX-020 Injectable Emulsion

|  | Analgesic Equivalent to Acetaminophen | | | Maximum Recommended | LD50** |
|---|---|---|---|---|---|
|  | 1x | 2x | 3x | CMX-020 Doses | CMX-020 Doses |
| Bolus | 0.01 mg/kg | 0.02 mg/kg | 0.04 mg/kg | 0.08 mg/kg | 2.4 mg/kg |
| Maintenance | 0.08 mg/kg/hr | 0.16 mg/kg/hr | 0.32 mg/kg/hr | 0.64 mg/kg/hr | 6.4 mg/kg/hr |
|  | For a 70 kg human: | | | For a 70 kg human: | For a 70 kg human: |
| Bolus | 0.6 mg | 1.4 mg | 2.8 mg | 5.6 mg | 170 mg |
| Maintenance | 6 mg/hr | 11 mg/hr | 23 mg/hr | 45 mg/hr | 450 mg/hr |

LD50 (abbreviation for "Lethal Dose, 50%") is established using mice. The dose translation between mouse and human is based on body surface area allometric translation. For example, a 1 mg/kg mouse dose is equivalent to a 0.08 mg/kg human dose. For more information on species dose translation see: Reagan-Shaw et. al, FASEB J. 122, 659-661 (2007).

pain indications. An important difference between the two assays is the strength of analgesic required to be effective in each of the assays. As seen below, to achieve a moderate level of efficacy, the tail-flick assay requires roughly 100x higher dose than the writhing assay from both CMX-020 and morphine. The administration of assays is described below.

Tail-Flick Assay in Mouse:

The tail-flick assay is based on the time measured to reflex withdrawal of the tail in response to a radiant heat source. The maximum exposure time to the radiant heat source is set at 10 seconds. Prior to treatment, a baseline (BL) time measured to tail-flick withdrawal is determined after two exposures to the radiant source separated by a 30 min period. Control mice are intravenously treated with vehicle and test mice are intravenously treated with analgesic test compound. Data of tail-flick withdrawal of treated mice (TM) are calculated as maximum possible effect (MPE), where $MPE=(TM-BL)/(10-BL)$. Tail-flick withdrawal is measured at 5 min, 15 min, 30 mm, and 1 hr. A total of 3-5 mice are used for each time point tested.

Writhing Assay in Mouse:

The writhing assay uses an injection of dilute acetic acid (0.55%) intraperitoneally which stimulates an internal pain response that results in writhing of the mouse. A writhe is indicated as a Whole body stretch or contraction of the abdomen. The mean number of writhes is counted over 5 min periods between 5-10 min, 15-20 min, 25-30 min, and 35-40 minutes after intravenous injection of either a test analgesic for treated mice (TM) or vehicle for baseline (BL). At each time point, data of writhing assay are calculated as maximum possible effect (MPE), where $MPE=(1-TM/BL)*100$. A total of 5 mice are used for each analgesic tested.

Tail-Flick Assay Performance Comparison—Bolus Injection.

Figure 4:
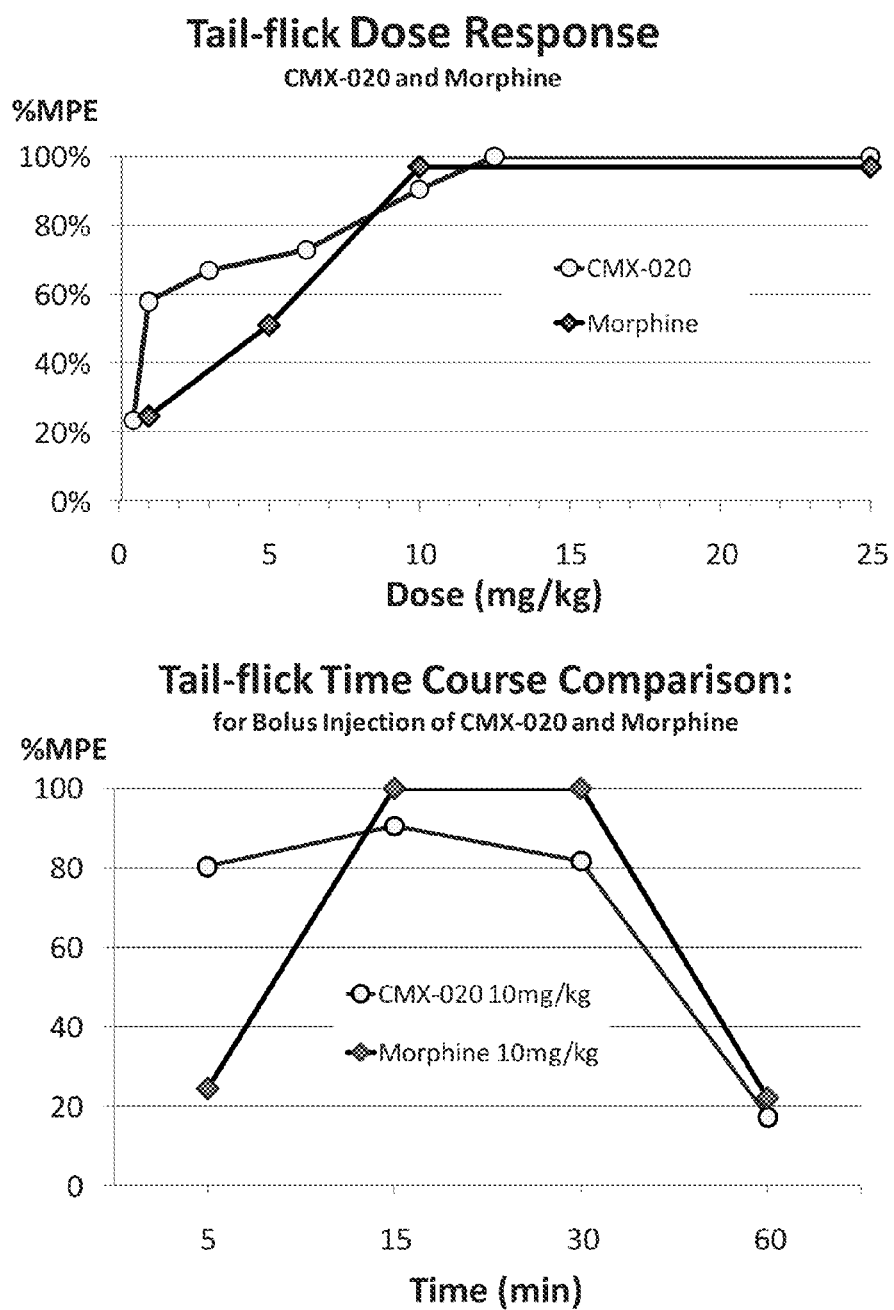
FIG. 4 provides dose response and time profile data for CMX-020 and morphine as measured in the Tail-flick Assay. At 100% MPE, graphs are separated to better distinguish.

In FIG. 4, the dose response of CMX-020 is delivered in its emulsion vehicle and compared with morphine; and the two compounds show very similar analgesic potency at the same doses. The time course comparison in FIG. 4 shows that CMX-020 acts very quickly, providing a maximal analgesic response at 5 minutes. The duration of this maximal CMX-020 response lasts through 30 minutes with a 10 mg/kg dose. At the same dose, morphine takes 15 minutes to establish its full analgesic effect. This effect also lasts through 30 minutes.

Writhing Assay Performance Comparison—Bolus Injection.

Figure 5:
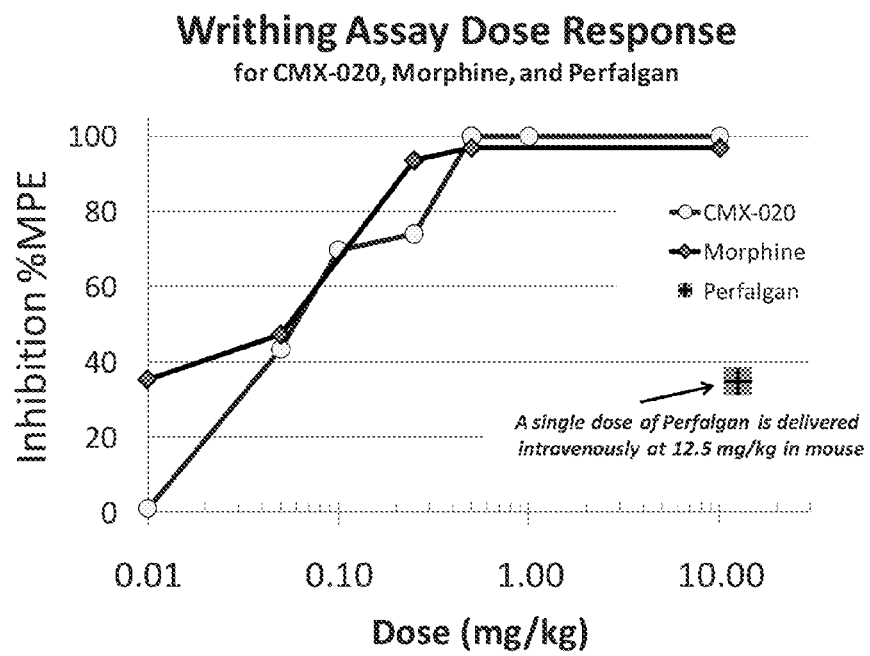
FIG. 5 depicts Writhing Assay data in terms of Bolus Dose Response and Infusion Comparison for CMX-020, Morphine, and Perfalgan. At 100% MPE, graphs are separated to better distinguish.
Figure 5:
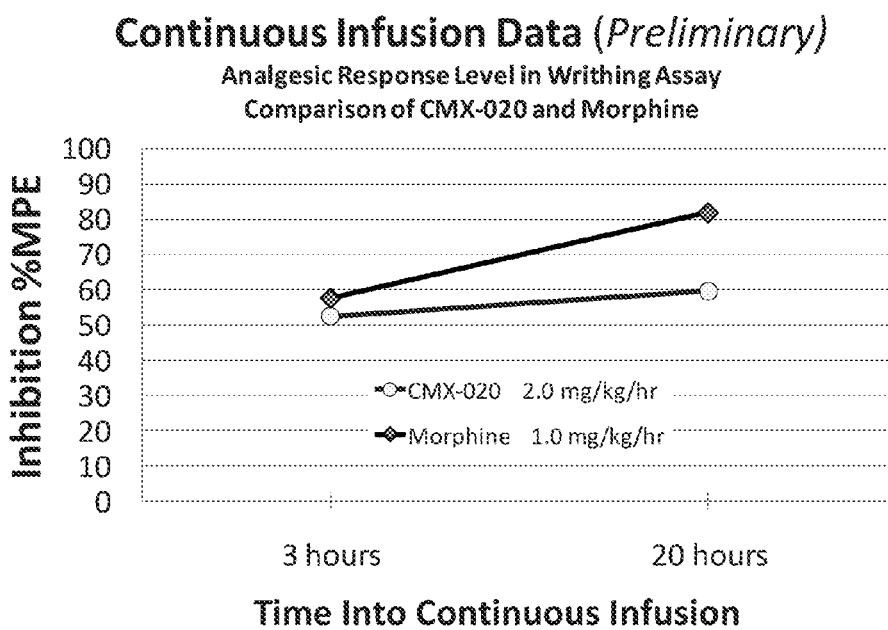

In the first graph of FIG. 5, the dose response of CMX-020 and morphine again show similar potency and both compounds achieve 100% MPE at a dose of approximately 0.5 mg/kg. With Perfalgan (intravenous acetaminophen), a 12.5 mg/kg dose establishes a relatively low, but measurable analgesic response of approximately 35% MPE. While only a single dose of Perfalgan is shown in the first graph, our tests show that the level of analgesia provide by Perfalgan does not increase above 35% MPE in the writhing assay for doses up to 200 mg/kg. At a dose of 0.05 mg/kg, CMX-020 provides a higher analgesic response than Perfalgan at a 12.5 mg/kg dose; here, the dose of Perfalgan is 250 times that of CMX-020.

Infusion Studies.

For patients requiring longer-term pain management, the continuous infusion of pain therapeutics enables the maintenance of constant levels of analgesia for long periods. In continuous infusion, a therapeutic is delivered in an infusion fluid at a constant flow rate through a peripheral venous catheter. The flow rate of infusion fluids can be controlled by either adjusting the drip rate, or more precisely, by using an infusion pump that also controls the total therapeutic dose delivered. In the second graph of FIG. 5, mice received an infusion of either CMX-020 or morphine over a 24 hour period. The infusion of CMX-020 and morphine utilizes a miniature therapeutic Alzet pump that is connected to a surgically implanted jugular vein cannula. This Alzet pump, which is implanted under the skin, administers a constant flow of therapeutic over 24 hours. Using the writhing assay, analgesic response levels are measured at 3 hours and 20 hours after beginning the continuous infusion. Doses of both CMX-020 and morphine were chosen so that analgesia levels were produced at roughly 50% MPE in the writhing assay. FIG. 5 shows preliminary results that utilize three to four animals for each time point and for controls. Several important conclusions can be made from this study. First, analgesia can be sustained at constant levels over a 24 hour period using continuous infusion. Analgesia levels in the second graph of FIG. 5 are greater than those provided by a 12.5 mg/kg dose of Perfalgan (acetaminophen). Second, the dose of CMX-020 required to maintain the approximate level of analgesia as morphine is only slightly higher: 2 mg/kg/hr of CMX-020 produces roughly the same level of analgesia as 1 mg/kg/hr of morphine. Higher infusion doses of both CMX-020 and morphine can be used to achieve much higher levels of analgesia.

As can be appreciated, CMX-020 is a fast-acting intravenous pain therapeutic that compares in potency and efficacy to morphine. In animal tests, the most significant difference between CMX-020 and morphine is how fast the compound acts. With CMX-020, the peak effect is reached within minutes; with morphine, the peak effect requires 15-40 minutes. In continuous infusions, CMX-020 and morphine sustain similar analgesic levels over 24 hours. While the required dose of CMX-020 is higher than morphine for continuous infusion, the added cost for a typical 6-10 mg CMX-020 dose for a 70 kg human would be a minimal.

The tail-flick and writhing assays represent different medical applications. The tail-flick assay represents severe acute pain applications, such as acute trauma, intensive care, and break-through pain. For severe acute pain applications CMX-020 requires higher doses. A prospective human dose for a 70 kg human for acute pain may be a 2.8 mg in a bolus injection for short-acting pain management, or 23.0 mg/hour in continuous infusions for longer term pain management. The writhing assay represents moderate pain applications, including those associated with post-operative pain management. CMX-020 may be administered at 0.6 mg in a bolus dose for short-acting applications, or 6.0 mg/hour in continuous infusions for longer term pain management. A comparable dose of acetaminophen is 1000 mg.

Example 4

Exemplary AA Analog Formulations for Analgesic Treatment

Preliminary tests show that CMX-020 is frilly functional when delivered using the emulsion vehicle formulation for Intralipid, as described in Table 5. Intralipid is used as an intravenous nutritional supplement and has market precedent for delivery of therapeutics such as Propofol (marketed by AstraZeneca). CMX-020 can also be prepared with emulsifying surfactants such as a lyophile, which is expected and typically used to provide long-tem storage and then is diluted in standard vehicle for injection. Preparation of these two vehicles is described below in Table 5.

TABLE 5

| Ingredients of Intralipid Formulation | |
|---|---|
| Quantities: | % (weight) |
| CMX-020 | 1% |
| soy bean oil | 10% |
| egg phosphatide | 1.20% |
| glycerol | 2.25% |
| disodium edetate dihydrate | 0.01% |
| sodium hydroxide (pH neutralizer) | q.s. |
| water for injections | to 100% |

Preparation of Intralipid Vehicle. Variation #1:

This variation has been demonstrated successfully by the inventors with CMX-020 in animal models. The Intralipid formulation is an oil-in-water emulsion. The ingredients for the Intralipid formulation that comprises 1% of CMX-020 by weight is shown in Table 5. Briefly, the preparation is as follows: The aqueous phase, comprising glycerol, disodium edetate dehydrate, sodium hydroxide, and water are mixed and filtered. In parallel, an oil phase comprising soy bean oil, CMX-020, and egg phosphatide is stirred, filtered and added to the aqueous phase via a static mixer. The mixture is then circulated through a high pressure homogenizer until a mean globule size of 250 nm is achieved. The emulsion is then filtered, filled into a container under nitrogen, and autoclaved. Variation #2: Since pure CMX-020 is itself a light oil, the soy bean oil is not necessary and is not included. In this formulation variation, CMX-020 would simply replace soy bean oil as an ingredient. This variation would enable much higher therapeutic concentrations in the same emulsion.

Preparation of Lyophile Vehicle.

The lyophile is an anhydrous emulsion composition that contains cryoprotection agents/bulking agents and can be redispersed by addition of water and give the original water containing emulsion with nearly identical particle size distribution. The emulsion composition is prepared by removing the aqueous phase by lyophilization, which is accomplished by freeze-drying.

Example 5

Exemplary AA Analog Pharmacokinetics

Preliminary Results of LC/MS Pharmacokinetics of CMX-020.

Figure 6:
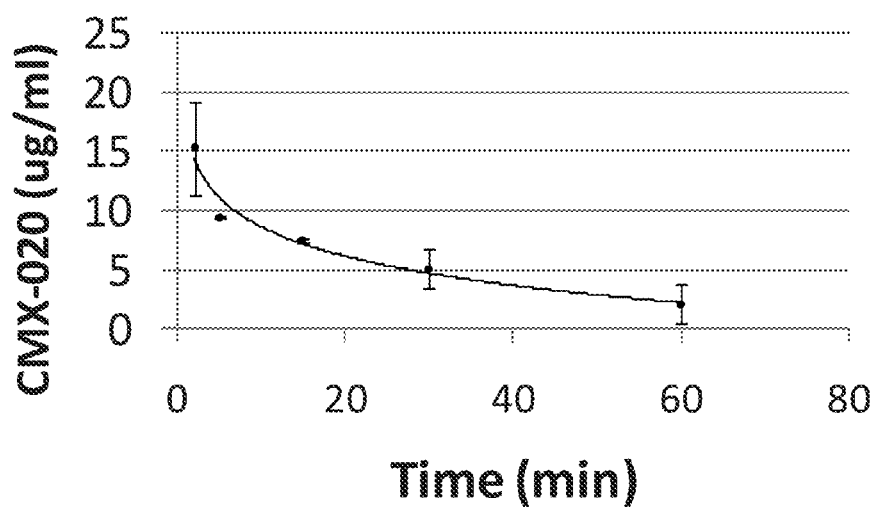
FIG. 6 provides CMX-020 Plasma Concentration in mouse measured by LC/MS.

Mice were injected in the tail vein with 10 mg/kg of CMX-020. Venous blood samples were collected at 2, 5, 15, 30 and 60 min following the injection of CMX-020. The blood samples were centrifuged to collect plasma and CMX-020 was extracted from 15 uL of plasma with chloroform:methanol (2: The extract was dried under a $N_2$ stream at room temperature, resuspended in mobile phase and quantified by LC/MS. As seen in FIG. 6, the concentration of CMX-020 in blood plasma falls with a half-life of approximately 17 minutes. Extrapolation hack to time zero represents an approximate plasma concentration of 14 ng/uL (or 33 uM). Samples of liver and brain were taken at 15 and 60 min after the single dose of CMX-020 was administered, homogenized and CMX-020 extracted as for plasma. The amount of CMX-020 present in brain was higher (704, 843 ng/g tissue, n=2) than that found in the liver (170, 211 ng/g tissue, n=2) at the 15 min timepoint. Less than 20 ng/g tissue of CMX-020 was found in both brain and liver at the 60 min timepoint. These results suggest that there is a preferential distribution of CMX-020 to the brain which is thought to be the primary target organ for mediating the analgesic effect.

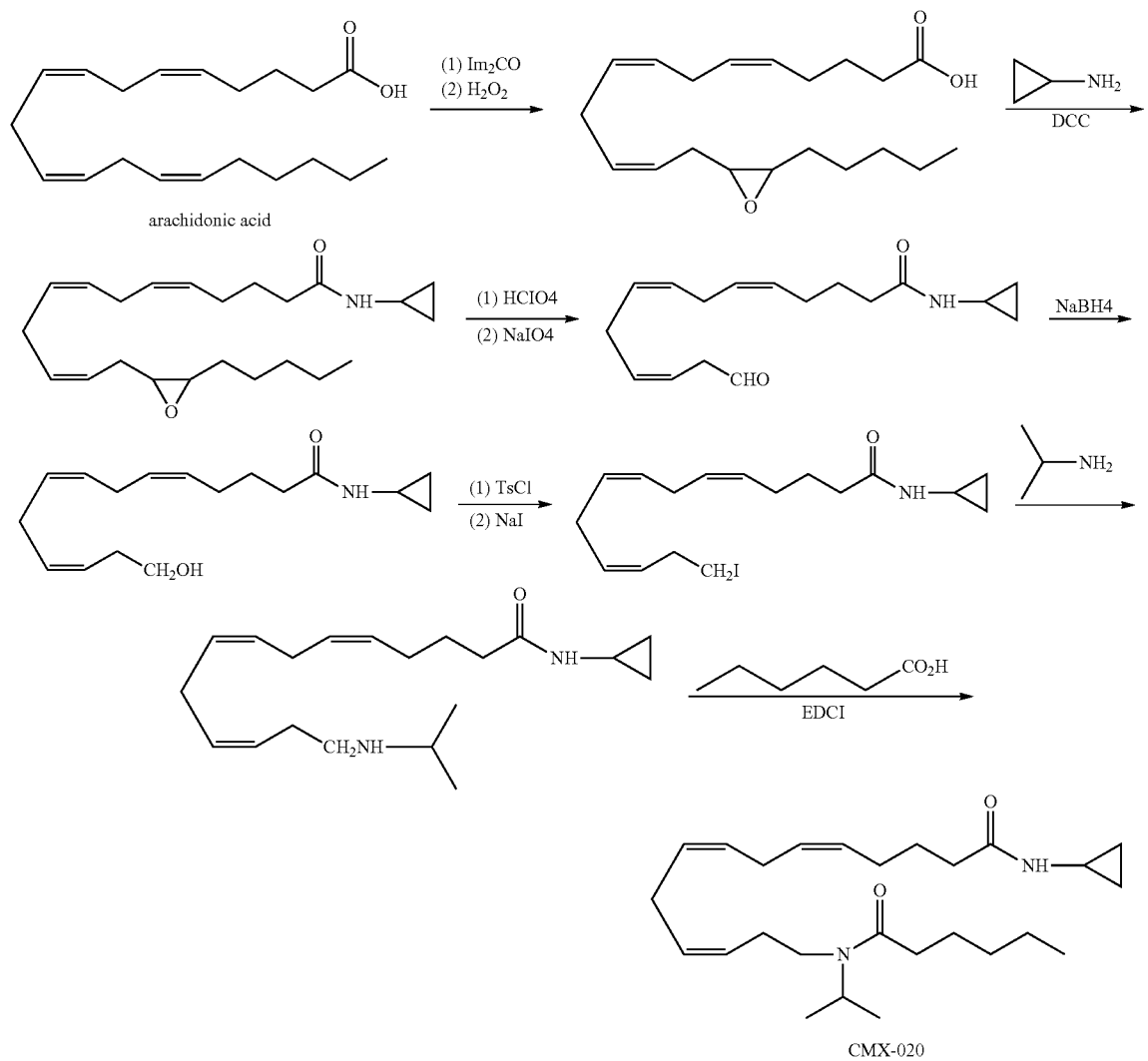

CMX-020

Example 6

Synthesis of AA Analogs from Arachidonic Acid

The present example illustrates a method of synthesizing AA analogs according to the invention starting from arachidonic acid. The below method yields the preferred compound CMX-020 but the method is suitable for providing related analogs through no more than routine optimization. (N,N-carbonyldiimidazole ("IM$_2$CO"); N,N'-dicyclohexylcarbodiimide ("DCC"))

Example 7

De Novo Synthesis of AA Analogs

The present example illustrates the de novo synthesis of AA analogs of the invention. The illustrated synthesis yields the preferred analog CMX-020 but the method is applicable to the manufacture of related compounds, including the compounds shown in FIG. 3, by no more than routine optimization.

Summary of CMX-020 De Novo Synthesis

Reaction A

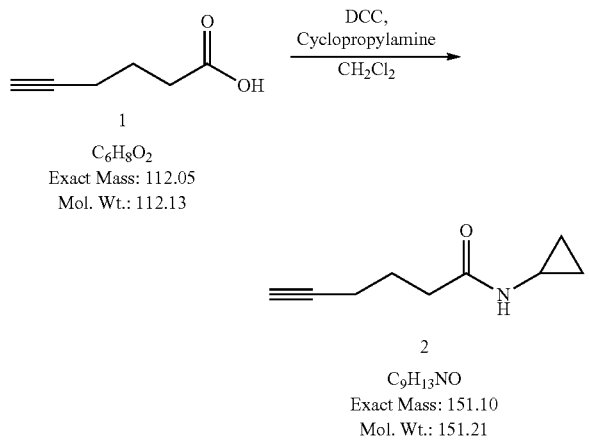

| | Materials | | | |
|---|---|---|---|---|
| | 5-Hexynoic acid | DCC | Cyclopropyl amine | CH$_2$Cl$_2$ |
| Source | GFS Cat#3197 | Aldrich Cat#D80002 | Aldrich Cat#125504 | Freshly distilled |
| Mol Wt | 112.13 | 206.33 | 57.09 | |
| Equiv | 1 | 1.5 | 1.1 | |
| Quantity | 5 g | 13.80 g | 2.80 g | 50 mL |
| mmol | 44.59 | 66.88 | 49.05 | |

To a stirred solution of 5-hexynoic acid (5 g, 44.59 mmol) anhydrous CH$_2$Cl$_2$ (50 ml) was added N,N'-dicyclohexylcarbodiimide ("DCC") (13.80 g, 66.88 mmol) followed by cyclopropylamine (2.80 g, 49.05 mmol) under an argon atmosphere at 0° C. After 2 h at 0° C., TLC of the reaction mixture showed completion reaction. The white precipitate was removed via filtration and the filtrate was concentrate under reduced pressure. The gummy residue was purified by SiO$_2$ column chromatography using Biotage pre-packed column (size: 100 g; solvent system: 10-75% EtOAc/hexane) to give pure amide 2 (6.54 g, 97%) as a white solid. Melting Point: 54.5-55.0° C.

Reaction B

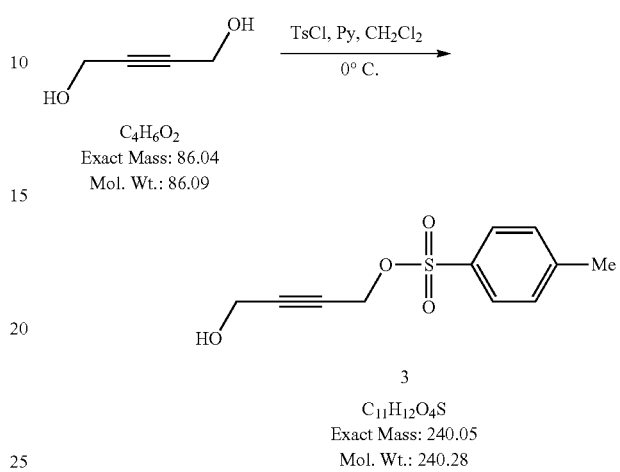

| | Materials | | | |
|---|---|---|---|---|
| | 2-Butyn-1,4-diol | Pyridine | TsCl | CH$_2$Cl$_2$ |
| Source | GFS Cat#80291 | Aldrich Cat# 270970 | Aldrich Cat#240877 | Freshly distilled |
| Mol Wt | 86.09 | 79.10 (d 0.978) | 190.65 | |
| Equiv | 1 | 2 | 1 | |
| Quantity | 10.00 g | 18.376 g (18.78 mL) | 22.145 g | 100 mL |
| mmol | 116.157 | 232.315 | 116.157 | |

To a stirring 0° C. solution of 2-butyn-1,4-diol (10.00 g, 116.157 mmol) in anhydrous CH$_2$Cl$_2$ (100 mL) was added anhydrous pyridine (18.276 g, 232.215 mmol) under an argon atmosphere. TsCl (22.145 g, 116.157 mmol) was then added portionwise over a period of 15 min. After stirring for another 1 h at 0° C., TLC of the reaction mixture revealed an approx. 70:30 ratio of mono and di-tosylate, but no starting diol. Water was added to quench the reaction. The CH$_2$Cl$_2$ layer was washed with water and CuSO$_4$ solution, then finally dried over anhydrous Na$_2$SO$_4$. After evaporation of the solvent, the crude product was purified by SiO$_2$ column chromatography using a Biotage pre-packed column (size: 340 g; solvent system: 10-50% EtOAc/hexane) to give pure mono-tosylate 3 (20.93 g, 75%) as a gummy semi-solid.

Reaction C

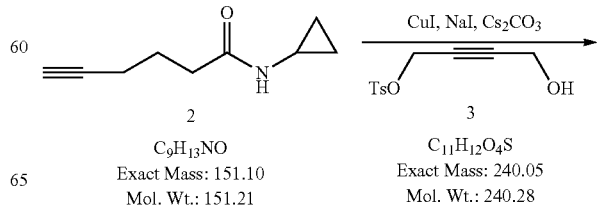

-continued

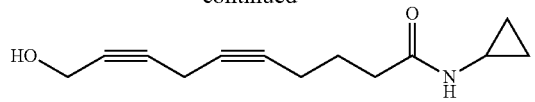

4
C₁₃H₁₇NO₂
Exact Mass: 219.13
Mol. Wt.: 219.28

| | Materials | | | |
|---|---|---|---|---|
| | 4 | TEA | MsCl | CH₂Cl₂ |
| Source | CRO Labs | Aldrich Cat#T0886 | Aldrich Cat#471259 | Freshly distilled |
| Mol Wt | 219.28 | 101.19 (d 0.726) | 114.55 (d 1.48) | |
| Equiv | 1 | 1.2 | 1.1 | |
| Quantity | 1.17 g | 0.647 g (0.89 mL) | 0.672 g (0.45 mL) | 25 mL |
| mmol | 5.335 | 6.402 | 5.869 | |

| | Materials | | | | | |
|---|---|---|---|---|---|---|
| | 2 | 3 | CuI | NaI | Cs₂CO₃ | DMF |
| Source | CRO Labs | CRO Labs | Aldrich Cat#205540 | Aldrich Cat#383112 | Aldrich Cat#441902 | Aldrich Cat#227056 |
| Mol Wt | 151.21 | 240.28 | 190.45 | 149.89 | 325.82 | |
| Equiv | 1.0 | 1.3 | 1.0 | 1.0 | 1.0 | |
| Quantity | 1.0 g | 2.06 g | 1.26 g | 0.99 g | 2.16 g | 50 mL |
| mmol | 6.613 | 8.603 | 6.613 | 6.613 | 6.613 | |

To a stirring, heterogeneous mixture of acetylene 2 (1.0 g, 6.613 mmol), CuI (1.26 g, 6.618 mmol), NaI (0.99 g, 6.618 mmol) and Cs₂CO₃ (2.16 g, 6.613 mmol) anhydrous DMF (50 mL) at 0° C. was added mono-tosylate 3 (2.07 g, 8.603 mmol) in DMF (2 mL) under an argon atmosphere. After stirring for 2 h at 0° C., the reaction mixture was allow to warm slowly to room temperature and stirred for another 24 h. The reaction mixture was diluted with ethyl acetate (200 mL) and a small amount of precipitate was removed via filtration. The filtrate was washed with water, brine and dried over anhydrous Na₂SO₄. After evaporation of the solvent, the residue was purified by SiO₂ column chromatography using a Biotage pre-packed column (size: 50 g; solvent system: 10-100% EtOAc/hexane) to give pure di-acetylene 4 (1.17 g, 81%).

Di-acetylene 4 is very sensitive to auto-oxidation. Store under argon in a non-polar solvent like hexane or toluene that is oxygen free. Use in next step as soon as practical.
Reaction D

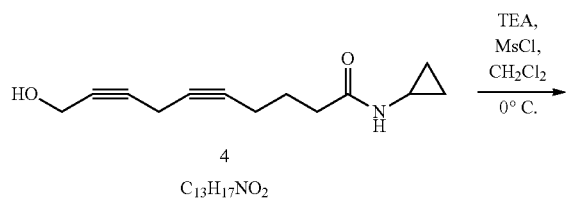

4
C₁₃H₁₇NO₂
Exact Mass: 219.13
Mol. Wt.: 219.28

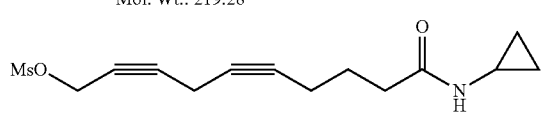

5
C₁₄H₁₉NO₄S
Exact Mass: 297.10
Mol. Wt.: 297.37

To a stirring, 0° C. solution of alcohol 4 (1.17 g, 5.335 mmol) in anhydrous CH₂Cl₂ (25 mL) was added Et₃N (0.647 g, 6.402 mmol) under an argon atmosphere. MsCl (0.672 g, 5.869 mmol) was then added dropwise via syringe over 15 min. After 1 h at 0° C. the reaction was quenched with water. The CH₂Cl₂ layer was washed with water and brine, then dried over anhydrous Na₂SO₄. After evaporation of the solvent, the residue was purified by SiO₂ column chromatography using a Biotage pre-packed column (size: 100 g; solvent system: 10-75% EtOAc/hexane) to give pure mesylate 5 (1.44 g, 91%) as an off white solid. Melting Point: 88.0-88.5° C. (decomposed)
Reaction E

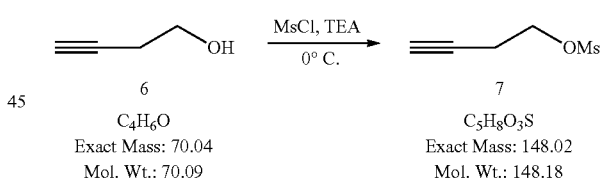

6
C₄H₆O
Exact Mass: 70.04
Mol. Wt.: 70.09

7
C₅H₈O₃S
Exact Mass: 148.02
Mol. Wt.: 148.18

| | Materials | | | |
|---|---|---|---|---|
| | 3-Butyn-1-ol | TEA | MsCl | CH₂Cl₂ |
| Source | Aldrich Cat#130850 | Aldrich Cat#T0886 | Aldrich Cat#471259 | Freshly distilled |
| Mol Wt | 70.09 | 101.19 (d 0.726) | 114.55 (d 1.48) | |
| Equiv | 1 | 1.5 | 1 | |
| Quantity | 10.0 g | 21.65 g (29.8 mL) | 16.34 g (11.04 mL) | 100 mL |
| mmol | 142.67 | 213.95 | 142.67 | |

To a stirring, 0° C. solution of 3-butyn-1-ol 6 (10.0 g, 142.67 mmol) anhydrous CH₂Cl₂ (100 mL) was added TEA (21.65 g, 213.95 mmol) under an argon atmosphere. MsCl (16.34 g, 11.04 mmol) was then added dropwise via syringe over a period of 15 min. After 1 h at 0° C., the reaction was quenched with water. The CH$_2$Cl$_2$ layer was washed with water and brine, then dried over anhydrous Na$_2$SO$_4$. After evaporation of the solvent, the residue was purified by SiO$_2$ column chromatography using a Biotage pre-packed column (size: 340 g; solvent system: 0-30% EtOAc/hexane) to give pure mesylate 7 (20.08 g, 95%).

Reaction F

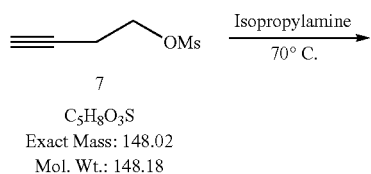

7
C$_5$H$_8$O$_3$S
Exact Mass: 148.02
Mol. Wt.: 148.18

C$_7$H$_{13}$N
Exact Mass: 111.10
Mol. Wt.: 111.18

| Materials | | | |
|---|---|---|---|
| | 7 | Isopropylamine | TEA |
| Source | CRO Labs | Aldrich Cat#320366 | Aldrich Cat#T0886 |
| Mol Wt | 148.18 | 59.11 | 101.19 (d 0.726) |
| Equiv | 1 | 1.5 | 1.5 |
| Quantity | 5.0 g | 2.99 g | 5.12 g (7.05 mL) |
| mmol | 33.74 | 50.61 | 50.61 |

Mesylate 7 (5.0 g, 33.74 mmol), isopropylamine (2.99 g, 50.61 mmol) and TEA (5.12 g, 7.05 mmol) were heated at 70° C. in a sealed tube. After for 3 h, the reaction mixture was concentration and the residue was dried under high vacuum to crude N-isopropylbut-3-yn-1-amine that was used in the next step without further purification.

Reaction G

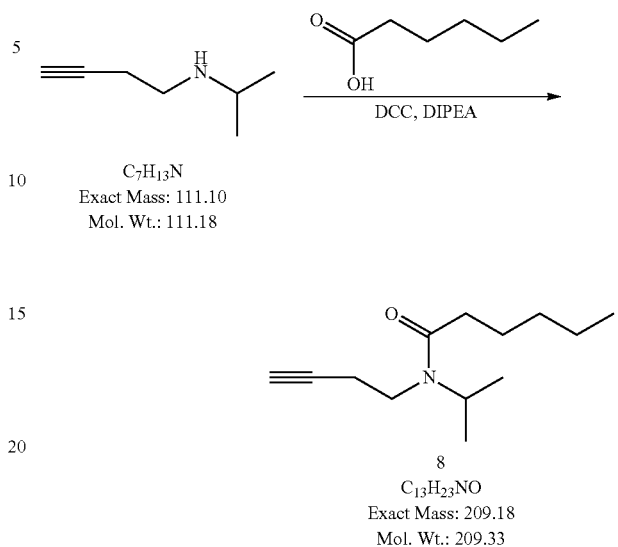

C$_7$H$_{13}$N
Exact Mass: 111.10
Mol. Wt.: 111.18

8
C$_{13}$H$_{23}$NO
Exact Mass: 209.18
Mol. Wt.: 209.33

| | Materials | | | |
|---|---|---|---|---|
| | Amine | Hexanoic acid | DCC | DIPEA |
| Source | Crude amine mixture from above | Aldrich Cat#12137 | Aldrich Cat#D80002 | Aldrich Cat# 387649 |
| Mol Wt | 111.18 (free amine) | 116.16 | 206.33 | 129.24 (d 0.742) |
| Quantity | 3.75 g crude | 3.917 g | 13.918 g | 17.43 g (23.5 mL) |

To a stirring, 0° C. solution of hexanoic acid (3.75 g, 33.72 mmol) in anhydrous CH$_2$Cl$_2$ (50 mL) was added DCC (13.918 g, 67.44 mmol) followed by addition of DIPEA (17.43 g, 84.43 mmol) and the crude N-isopropylbut-3-yn-1-amine (3.75 g, 33.72 mmol) from aboveunder an argon atmosphere. After stirring for 2 h at 0° C., the white precipitate was removed via filtration. The filtrate was concentrate under reduced pressure, the gummy residue was purified by SiO$_2$ column chromatography using a Biotage pre-packed column (size: 100 g; solvent system: 0-40% EtOAc/hexane) to give pure amide 8 (6.42 g) as a viscous oil.

Reaction H

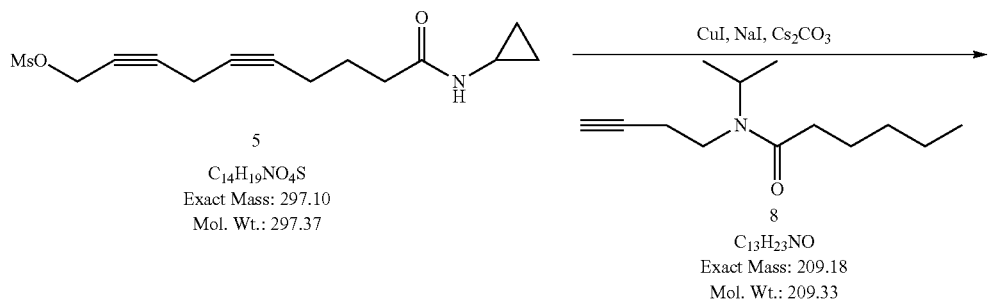

5
C$_{14}$H$_{19}$NO$_4$S
Exact Mass: 297.10
Mol. Wt.: 297.37

8
C$_{13}$H$_{23}$NO
Exact Mass: 209.18
Mol. Wt.: 209.33

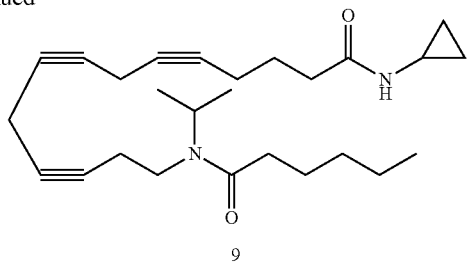

9

C$_{26}$H$_{38}$N$_2$O$_2$
Exact Mass: 410.29
Mol. Wt.: 410.59

| Materials | | | | | |
|---|---|---|---|---|---|
| | 5 | 8 | CuI | NaI | Cs$_2$CO$_3$ | DMF |
| Source | CRO Labs | CRO labs | Aldrich Cat#205540 | Aldrich Cat#383112 | Aldrich Cat#441902 | Aldrich Cat#227056 |
| Mol Wt | 297.37 | 209.33 | 190.45 | 149.89 | 325.82 | |
| Equiv | 1.0 | 1.0 | 1.0 | 1.0 | 1.0 | |
| Quantity | 1.2 g | 0.844 g | 0.768 g | 0.604 g | 1.314 g | 50 mL |
| mmol | 4.035 | 4.035 | 4.035 | 4.035 | 4.035 | |

To a stirring, 0° C. heterogeneous mixture of acetylene 8 (0.844 g, 4.035 mmol), CuI (0.768 g, 4.035 mmol), NaI (0.604 g, 4.035 mmol) and Cs$_2$CO$_3$ (1.314 g, 4.035 mmol) in anhydrous DMF (50 nit) was added a solution of mesylate 5 (1.2 g, 4.035 mmol) in DMF (5 mL) under an argon atmosphere. After stirring for 2 h at 0° C., the reaction mixture was slowly warmed to room temperature and stirred for an additional 24 h. The reaction mixture was then diluted with ethyl acetate (200 mL) the precipitated mass was removed via filtration. The filtrate was washed with water, brine, dried over anhydrous Na$_2$SO$_4$, and evaporation in vacuo. The residue was purified by SiO$_2$ column chromatography using a Biotage pre-packed column (size: 100 g; solvent system: 10-75% EtOAc/hexane) to give tris-acetylene 9 (1.3 g, 89%) as a pale yellow oil which was used in the next step as early as possible.

Tris-acetylene 9 is extremely sensitive to auto-oxidation. Store under argon in a non-polar solvent like hexane or toluene that is oxygen free:

Reaction I

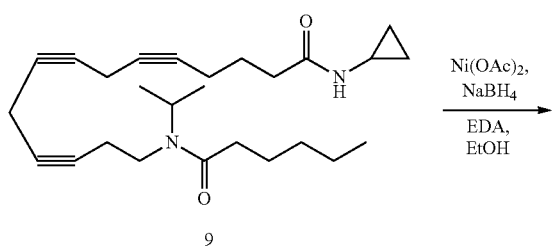

9

C$_{26}$H$_{38}$N$_2$O$_2$
Exact Mass: 410.29
Mol. Wt.: 410.59

-continued

CMX-020

C$_{26}$H$_{44}$N$_2$O$_2$
Exact Mass: 416.34
Mol. Wt.: 416.64

| Materials | | | | |
|---|---|---|---|---|
| | Triacetylene 9 | Ni(OAc)$_2$·4H$_2$O | NaBH$_4$ | EDA |
| Source | CRO labs | RM7H21 | Aldrich | Fluka |
| Mol Wt | 410.59 | 248.86 | 37.83 | 60.1 (d 0.897) |
| Equiv | 1 | 2 | 2 | 9 |
| Quantity | 0.50 g | 0.606 g | 0.092 g | 0.658 g (0.73 mL) |
| mmol | 1.217 | 2.435 | 2.43 | 10.948 |

To a stirring, room temperature solution of nickel acetate tetra-hydrate (0.606 g, 2.435 mmol) in absolute EtOH (5 mL) was added solid NaBH$_4$ (0.092 g, 2.43 mmol) under a H$_2$ atmosphere (balloon~1 atm). The resulting black suspension was stirred for 30 min, then distilled ethylenediamine (0.658 g, 10.948 mmol) was added via syringe. Following complete addition, the suspension was stirred for another 15 min, then triacetylene 9 (0.50 g, 1.217 mmol) in absolute EtOH (5 mL) was added. After stirring at room temperature under H$_2$ (balloon~1 atm) for 3 h, TLC showed completion of the reaction. Diethyl ether (50 mL) was added to dilute the reaction mixture that was then passed through a short silica gel column to remove catalyst and ethylenediamine. The filtrate was concentrated under reduced pressure and concentrated in vacuo. The residue was purified by flash column chromatography (0-75% ethyl acetate/hexanes) to give CMX-020 as a colorless oil (91%). HPLC analysis (C18, 70/30 acetonitrile/$H_2O$) of this product showed about 10% of over saturated product, which was further purified by prep HPLC to give CMX-202 as a 99% pure product as a viscous oil. CMX-020 is stored under argon at −20° C. or −80° C.

An alternative reduction procedure is shown and described below.

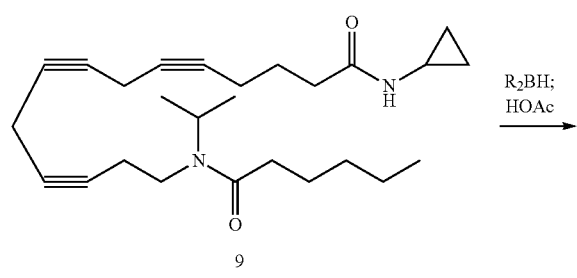

Anhydrous methyl tert-butyl ether (MTBE, 40 mL) was transferred to a 250 mil, flask followed by borane dimethylsulide complex (2.96 g) under an argon atmosphere. The solution was cooled to 0-5° C. Cyclohexene (6.4 g) was added with stirring at a rate as to keep the temperature of the reaction mixture below 10° C. After complete addition, the reaction mixture was stirred for an additional 2 h at 0-5° C. A solution of intermediate 9 in anhydrous MTBE (10 mL) was added, again at a rate that kept the temperature below 10° C. The reaction mixture was stirred for an additional 2 h at 0-5° C. at which time HPLC analysis indicated all of the starting material had reacted. The reaction mixture was quenched by the slow addition of acetic acid (20 mL) at a rate that kept the temperature of the reaction mixture below 20° C. After complete addition of the acetic acid, the mixture was stirred at room temperature for 30 min, then the MTBE was removed in vacuo. The remaining material was stirred at room temperature for 30 min, then partitioned between water and MTBE. The combined organic extracts were washed with water, cooled to 0-5° C., and 6N aq. NaOH solution (50 mL) was added followed by 30 wt % $H_2O_2$ (12 mL). After stirring at room temperature for 1 h, the organic phase was separated, washed with aq. sodium thiosulfate (10 wt %), dried, evaporated under reduced pressure. The residue was purified using a silica gel column eluted with 30-70% EtOAc/hexanes to give CMX-020 (49%) as a colorless oil.

Example 8

Antipyretic Effect of CMX-020

Figure 7:
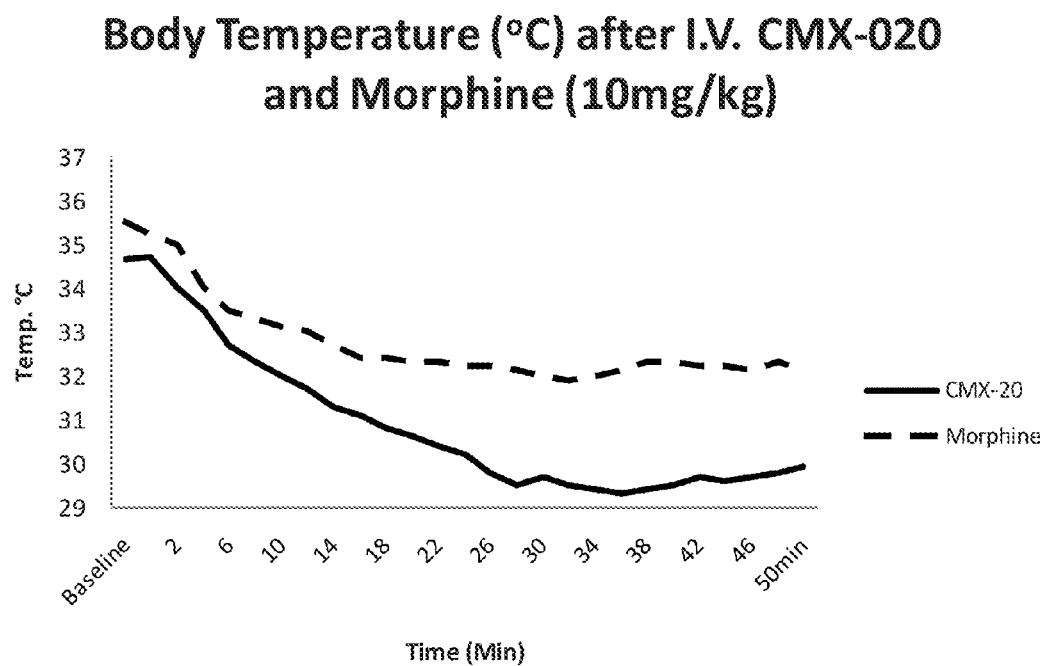
FIG. 7 illustrates the antipyretic (i.e., fever reducing) effect of compound CMX-020 as compared to morphine in mice.

This example demonstrates the antipyretic effect of compound CMX-020 as compared to morphine. Recordings of body temperature in male mice (30 grams) were achieved using a mouse rectal temperature probe. Baseline was recorded twice for 10 minutes at intervals of 2 minutes with a 15 minute span of no recording. After an i.v. bolus injection of either CMX-020 (10 mg/kg) or morphine (10 mg/kg) body temperature was recorded every 2 minutes for 50 minutes. FIG. 7 illustrates the antipyretic effect of compound CMX-020 as compared to morphine.

Example 9

De Novo Synthesis of Additional AA Analogs—CMX-020 Variants

This example provides a synthetic route to an exemplary AA analog structurally-similar to CMX-020. Such chemical variants may be synthesized by routine chemical modification after review and appreciation of the present disclosure.

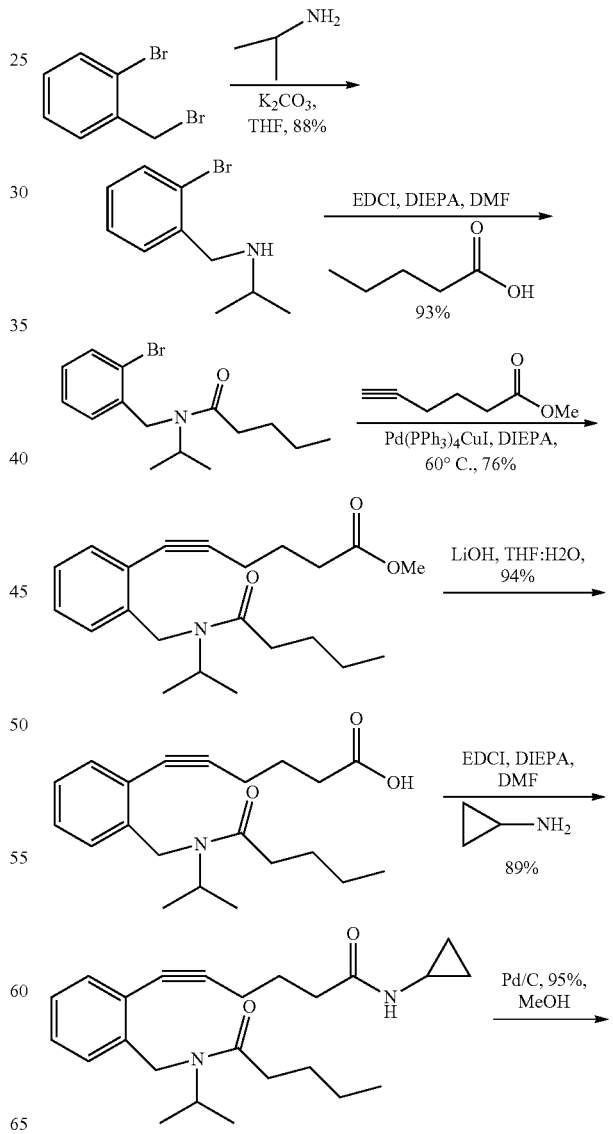

-continued

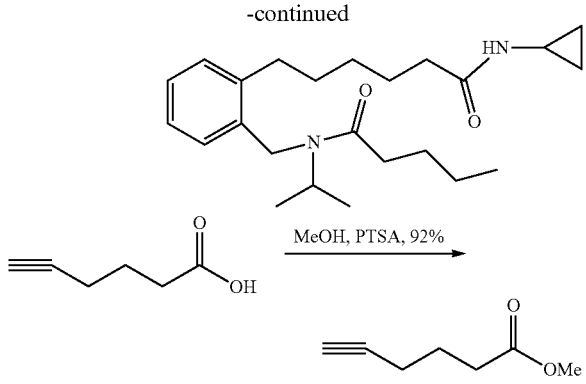

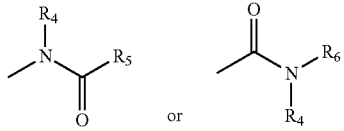

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A compound having the structure:

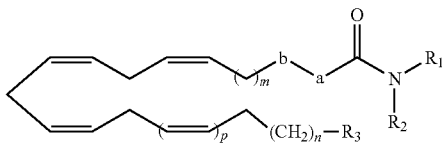

wherein:
R$_1$ is H, or a C$_1$-C$_6$ alkyl, C$_3$-C$_6$ alkenyl, C$_3$-C$_6$ cycloalkyl or C$_3$-C$_6$ cycloalkenyl which is unsubstituted or substituted with a hydroxyl group or a C$_1$-C$_6$ alky;

R$_2$ is H, or a C$_1$-C$_3$ alkyl; or R$_1$ and R$_2$ form a C$_3$-C$_6$ heterocyclic ring with the nitrogen bonded to said R$_1$ and R$_2$;

R$_3$ is:

in which:
R$_4$ is H, or a C$_1$-C$_6$ alkyl, C$_3$-C$_6$ alkenyl, C$_3$-C$_6$ cycloalkyl or C$_3$-C$_6$ cycloalkenyl;

R$_5$ is a C$_1$-C$_6$ alkyl, C$_1$-C$_6$ alkoxy, or C$_2$-C$_6$ alkyl ether which is unsubstituted or substituted with one or more of hydroxyl, phenyl, phenyloxy, or fluorine, or R$_5$ is NR$_7$R$_8$, or C(O)NR$_7$R$_8$ in which R$_7$ and R$_8$ are independently selected from H, a C$_1$-C$_6$ alkyl, C$_3$-C$_6$ alkenyl, C$_3$-C$_6$ cycloalkyl or C$_3$-C$_6$ cycloalkenyl;

R$_6$ is H, or a C$_1$-C$_6$ alkyl, C$_3$-C$_6$ alkenyl, C$_3$-C$_6$ cycloalkyl or C$_3$-C$_6$ cycloalkenyl;

n is 0, 1, 2, 3, or 4;

position a is —CH$_2$—, —C(CH$_3$)—, —C(CH$_3$)$_2$—, O or NR$_9$ where R$_9$ is H, OH, or a C$_1$-C$_6$ alkyl;

position b is —CH$_2$—, —CH(CH$_3$)—, —C(CH$_3$)$_2$—, O, S, or NR$_{10}$ where R$_{10}$ is H, OH, or a C$_1$-C$_6$ alkyl; wherein position a and b are not both heteroatoms;

m is 0, 1, 2, 3, or 4; wherein when m is 0, then position b is a carbon;

p is 1, 2, or 3; or a pharmaceutically acceptable salt thereof.

2. A composition comprising a compound according to claim 1 and a pharmaceutically acceptable carrier.

3. A method of providing analgesia to a subject, comprising administering to a subject a therapeutically effective amount of a compound according to claim 1, whereby analgesia is provided in said subject.

4. A method of reducing fever in a subject, comprising administering to a subject a therapeutically effective amount of a compound according to claim 1, whereby fever is reduced in said subject.

* * * * *